(12) United States Patent
Matthews

(10) Patent No.: US 12,226,309 B2
(45) Date of Patent: *Feb. 18, 2025

(54) INTRAOCULAR LENS STORAGE AND LOADING DEVICES AND METHODS OF USE

(71) Applicant: Alcon Inc., Fribourg (CH)

(72) Inventor: Gregory Vinton Matthews, San Francisco, CA (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/470,324

(22) Filed: Sep. 19, 2023

(65) Prior Publication Data
US 2024/0008974 A1    Jan. 11, 2024

Related U.S. Application Data

(63) Continuation of application No. 17/357,463, filed on Jun. 24, 2021, now Pat. No. 11,793,627, which is a continuation of application No. 16/268,280, filed on Feb. 5, 2019, now Pat. No. 11,071,622, which is a continuation of application No. 14/776,752, filed as application No. PCT/US2014/030353 on Mar. 17, 2014, now Pat. No. 10,195,020.

(60) Provisional application No. 61/799,755, filed on Mar. 15, 2013.

(51) Int. Cl.
*A61F 2/16* (2006.01)
*A61F 9/007* (2006.01)

(52) U.S. Cl.
CPC ............ *A61F 2/1678* (2013.01); *A61F 2/167* (2013.01); *A61F 9/007* (2013.01)

(58) Field of Classification Search
CPC ...... A61F 2/148; A61F 2/1662; A61F 2/1667; A61F 2/167; A61F 2/1672; A61F 2/1675; A61F 2/1678; A61F 2/1691; A61F 9/007; A61F 2002/1681
See application file for complete search history.

(56) References Cited

U.S. PATENT DOCUMENTS

| | | |
|---|---|---|
| 2,990,670 A | 7/1961 | Kingsbury |
| 4,253,199 A | 3/1981 | Banko |
| 4,273,109 A | 6/1981 | Enderby |
| 4,298,996 A | 11/1981 | Barnet |
| 4,304,895 A | 12/1981 | Loshaek |
| 4,423,809 A | 1/1984 | Mazzocco |
| 4,435,855 A | 3/1984 | Pannu |
| 4,461,294 A | 7/1984 | Baron |

(Continued)

FOREIGN PATENT DOCUMENTS

| | | |
|---|---|---|
| CN | 1200659 | 12/1998 |
| CN | 1283974 | 2/2001 |

(Continued)

OTHER PUBLICATIONS

Baughman et al. "Negative poisson's ratios for extreme states of matter," *Science*, vol. 288, pp. 2018-2022, Jun. 16, 2000.

(Continued)

*Primary Examiner* — Ryan J. Severson
(74) *Attorney, Agent, or Firm* — Levine Bagade Han LLP

(57) ABSTRACT

Intraocular lens loading devices and methods of use. In some embodiment the devices are used to sequentially splay first and second haptics while loading the intraocular lens into a delivery lumen.

20 Claims, 18 Drawing Sheets

(56) References Cited

U.S. PATENT DOCUMENTS

| | | |
|---|---|---|
| 4,466,705 A | 8/1984 | Michelson |
| 4,490,860 A | 1/1985 | Rainin |
| 4,494,254 A | 1/1985 | Lopez |
| 4,512,040 A | 4/1985 | Mcclure |
| 4,528,311 A | 7/1985 | Beard et al. |
| 4,538,608 A | 9/1985 | L'esperance |
| 4,558,698 A | 12/1985 | O'dell |
| 4,566,438 A | 1/1986 | Liese et al. |
| 4,604,087 A | 8/1986 | Joseph |
| 4,617,715 A | 10/1986 | Koistinen et al. |
| 4,633,866 A | 1/1987 | Peyman et al. |
| 4,634,418 A | 1/1987 | Binder |
| 4,658,816 A | 4/1987 | Ector |
| 4,685,921 A | 8/1987 | Peyman |
| 4,685,922 A | 8/1987 | Peyman |
| 4,693,717 A | 9/1987 | Michelson |
| 4,722,350 A | 2/1988 | Armeniades et al. |
| 4,722,724 A | 2/1988 | Schocket |
| 4,729,373 A | 3/1988 | Peyman |
| 4,731,079 A | 3/1988 | Stoy |
| 4,733,665 A | 3/1988 | Palmaz |
| 4,750,901 A | 6/1988 | Molteno |
| 4,770,654 A | 9/1988 | Rogers et al. |
| 4,781,719 A | 11/1988 | Kelman |
| 4,784,485 A | 11/1988 | Ho |
| 4,790,847 A | 12/1988 | Woods |
| 4,791,927 A | 12/1988 | Menger |
| 4,816,031 A | 3/1989 | Pfoff |
| 4,819,631 A | 4/1989 | Poley |
| 4,826,478 A | 5/1989 | Schocket |
| 4,836,201 A | 6/1989 | Patton et al. |
| 4,842,601 A | 6/1989 | Smith |
| 4,848,343 A | 7/1989 | Wallsten et al. |
| 4,861,341 A | 8/1989 | Woodburn |
| 4,863,457 A | 9/1989 | Lee |
| 4,876,250 A | 10/1989 | Clark |
| 4,880,000 A | 11/1989 | Holmes et al. |
| 4,886,488 A | 12/1989 | White |
| 4,892,543 A | 1/1990 | Turley |
| 4,902,293 A | 2/1990 | Feaster |
| 4,906,247 A | 3/1990 | Fritch |
| 4,911,714 A | 3/1990 | Poley |
| 4,917,680 A | 4/1990 | Poley |
| 4,925,299 A | 5/1990 | Meisberger et al. |
| 4,934,363 A | 6/1990 | Smith et al. |
| 4,934,809 A | 6/1990 | Volk |
| 4,946,436 A | 8/1990 | Smith |
| 4,946,469 A | 8/1990 | Sarfarazi |
| 4,950,289 A | 8/1990 | Krasner |
| 4,955,889 A | 9/1990 | Van Gent |
| 4,963,148 A | 10/1990 | Sulc et al. |
| 4,968,296 A | 11/1990 | Ritch et al. |
| 4,988,352 A | 1/1991 | Poley |
| 4,994,060 A | 2/1991 | Rink et al. |
| 4,995,880 A | 2/1991 | Galib |
| 5,007,510 A | 4/1991 | Houng |
| 5,007,913 A | 4/1991 | Dulebohn et al. |
| 5,035,710 A | 7/1991 | Nakada et al. |
| 5,041,081 A | 8/1991 | Odrich |
| 5,047,051 A | 9/1991 | Cumming |
| 5,061,914 A | 10/1991 | Busch et al. |
| 5,066,301 A | 11/1991 | Wiley |
| 5,092,837 A | 3/1992 | Ritch et al. |
| 5,100,410 A | 3/1992 | Dulebohn |
| 5,108,429 A | 4/1992 | Wiley |
| 5,123,902 A | 6/1992 | Muller et al. |
| 5,123,905 A | 6/1992 | Kelman |
| 5,127,901 A | 7/1992 | Odrich |
| 5,129,895 A | 7/1992 | Vassiliadis et al. |
| 5,145,935 A | 9/1992 | Hayashi |
| 5,152,789 A | 10/1992 | Willis |
| 5,171,241 A | 12/1992 | Buboltz et al. |
| 5,171,266 A | 12/1992 | Wiley et al. |
| 5,180,362 A | 1/1993 | Worst |
| 5,200,430 A | 4/1993 | Federman |
| 5,201,763 A | 4/1993 | Brady et al. |
| 5,213,579 A | 5/1993 | Yamada et al. |
| 5,235,003 A | 8/1993 | Ward et al. |
| 5,238,004 A | 8/1993 | Sahatjian et al. |
| 5,251,993 A | 10/1993 | Sigourney |
| 5,254,112 A | 10/1993 | Sinofsky et al. |
| 5,275,623 A | 1/1994 | Sarfarazi |
| 5,275,624 A | 1/1994 | Hara et al. |
| 5,288,293 A | 2/1994 | O'donnell |
| 5,300,020 A | 4/1994 | L'esperance |
| 5,304,182 A | 4/1994 | Rheinish et al. |
| 5,326,347 A | 7/1994 | Cumming |
| 5,342,370 A | 8/1994 | Simon et al. |
| 5,354,333 A | 10/1994 | Kammann et al. |
| 5,360,399 A | 11/1994 | Stegmann |
| 5,372,577 A | 12/1994 | Ungerleider |
| 5,391,590 A | 2/1995 | Gerace et al. |
| 5,426,166 A | 6/1995 | Usifer et al. |
| 5,433,701 A | 7/1995 | Rubinstein |
| 5,443,505 A | 8/1995 | Wong et al. |
| 5,444,135 A | 8/1995 | Cheradame et al. |
| 5,445,637 A | 8/1995 | Bretton |
| 5,454,746 A | 10/1995 | Guegan et al. |
| 5,454,796 A | 10/1995 | Krupin |
| 5,468,246 A | 11/1995 | Blake |
| 5,476,514 A | 12/1995 | Cumming |
| 5,489,302 A | 2/1996 | Skottun |
| 5,496,366 A | 3/1996 | Cumming |
| 5,549,614 A | 8/1996 | Tunis |
| 5,558,630 A | 9/1996 | Fisher |
| 5,562,676 A | 10/1996 | Brady et al. |
| 5,575,780 A | 11/1996 | Saito |
| 5,578,081 A | 11/1996 | Mcdonald |
| 5,585,049 A | 12/1996 | Grisoni et al. |
| 5,591,223 A | 1/1997 | Lock et al. |
| 5,593,436 A | 1/1997 | Langerman |
| 5,607,472 A | 3/1997 | Thompson |
| 5,618,903 A | 4/1997 | Hoxmeier et al. |
| 5,620,450 A | 4/1997 | Eagles et al. |
| 5,626,559 A | 5/1997 | Solomon |
| 5,628,795 A | 5/1997 | Langerman |
| 5,633,504 A | 5/1997 | Collins et al. |
| 5,643,276 A | 7/1997 | Zaleski |
| 5,651,782 A | 7/1997 | Simon et al. |
| 5,653,715 A | 8/1997 | Reich et al. |
| 5,653,753 A | 8/1997 | Brady et al. |
| 5,665,822 A | 9/1997 | Bitler et al. |
| 5,676,669 A | 10/1997 | Colvard |
| 5,676,944 A | 10/1997 | Alvarado et al. |
| 5,684,637 A | 11/1997 | Floyd |
| 5,697,973 A | 12/1997 | Peyman et al. |
| 5,702,400 A | 12/1997 | Brown et al. |
| 5,702,414 A | 12/1997 | Richter et al. |
| 5,704,907 A | 1/1998 | Nordquist et al. |
| 5,713,844 A | 2/1998 | Peyman |
| 5,735,858 A | 4/1998 | Makker et al. |
| 5,736,491 A | 4/1998 | Patel et al. |
| 5,738,676 A | 4/1998 | Hammer et al. |
| 5,738,677 A | 4/1998 | Colvard et al. |
| 5,741,292 A | 4/1998 | Mendius |
| 5,767,669 A | 6/1998 | Hansen et al. |
| 5,774,273 A | 6/1998 | Bornhorst |
| 5,776,138 A | 7/1998 | Vidal et al. |
| 5,785,658 A | 7/1998 | Benaron et al. |
| 5,792,103 A | 8/1998 | Schwartz et al. |
| 5,803,925 A | 9/1998 | Yang et al. |
| 5,807,244 A | 9/1998 | Barot |
| 5,807,302 A | 9/1998 | Wandel |
| 5,811,453 A | 9/1998 | Yanni et al. |
| 5,843,188 A | 12/1998 | Mcdonald |
| 5,868,697 A | 2/1999 | Richter et al. |
| 5,868,751 A | 2/1999 | Feingold |
| 5,873,879 A | 2/1999 | Figueroa et al. |
| RE36,150 E | 3/1999 | Gupta |
| 5,885,279 A | 3/1999 | Bretton |
| 5,891,931 A | 4/1999 | Leboeuf et al. |
| 5,893,837 A | 4/1999 | Eagles et al. |
| 5,919,171 A | 7/1999 | Kira et al. |
| 5,921,918 A | 7/1999 | Riza |

(56) References Cited

U.S. PATENT DOCUMENTS

| | | | |
|---|---|---|---|
| 5,928,282 | A | 7/1999 | Nigam |
| 5,947,974 | A | 9/1999 | Brady et al. |
| 5,984,962 | A | 11/1999 | Anello et al. |
| 5,984,963 | A | 11/1999 | Ryan et al. |
| 5,990,099 | A | 11/1999 | Clark |
| 5,993,438 | A | 11/1999 | Juhasz et al. |
| 5,997,531 | A | 12/1999 | Loeb et al. |
| 6,001,107 | A | 12/1999 | Feingold |
| 6,002,480 | A | 12/1999 | Izatt et al. |
| 6,007,510 | A | 12/1999 | Nigam |
| 6,022,358 | A | 2/2000 | Wolf et al. |
| 6,036,678 | A | 3/2000 | Giungo |
| 6,048,348 | A | 4/2000 | Chambers et al. |
| 6,050,970 | A | 4/2000 | Baerveldt |
| 6,050,999 | A | 4/2000 | Paraschac et al. |
| 6,083,193 | A | 7/2000 | Kadziauskas et al. |
| 6,102,045 | A | 8/2000 | Nordquist et al. |
| 6,102,539 | A | 8/2000 | Tucker |
| 6,129,733 | A | 10/2000 | Brady et al. |
| 6,139,576 | A | 10/2000 | Doyle et al. |
| 6,140,438 | A | 10/2000 | Ojio et al. |
| 6,146,375 | A | 11/2000 | Juhasz et al. |
| 6,152,918 | A | 11/2000 | Padilla et al. |
| 6,179,843 | B1 | 1/2001 | Weiler |
| 6,186,974 | B1 | 2/2001 | Allan et al. |
| 6,188,526 | B1 | 2/2001 | Sasaya et al. |
| 6,195,807 | B1 | 3/2001 | Chou |
| 6,197,059 | B1 | 3/2001 | Cumming |
| 6,200,342 | B1 | 3/2001 | Tassignon |
| 6,203,513 | B1 | 3/2001 | Yaron et al. |
| 6,217,584 | B1 | 4/2001 | Nun |
| 6,217,612 | B1 | 4/2001 | Woods |
| 6,225,367 | B1 | 5/2001 | Chaouk et al. |
| 6,229,641 | B1 | 5/2001 | Kosaka |
| 6,238,409 | B1 | 5/2001 | Hojeibane |
| 6,251,090 | B1 | 6/2001 | Avery et al. |
| 6,251,114 | B1 | 6/2001 | Farmer et al. |
| 6,280,449 | B1 | 8/2001 | Blake |
| 6,283,975 | B1 | 9/2001 | Glick et al. |
| 6,283,976 | B1 | 9/2001 | Portney |
| 6,299,641 | B1 | 10/2001 | Woods |
| 6,312,433 | B1 | 11/2001 | Butts et al. |
| 6,336,932 | B1 | 1/2002 | Figueroa et al. |
| 6,342,073 | B1 | 1/2002 | Cumming et al. |
| 6,371,960 | B2 | 4/2002 | Heyman et al. |
| 6,375,642 | B1 | 4/2002 | Grieshaber et al. |
| 6,387,101 | B1 | 5/2002 | Butts et al. |
| 6,388,043 | B1 | 5/2002 | Langer et al. |
| 6,398,789 | B1 | 6/2002 | Capetan |
| 6,406,481 | B2 | 6/2002 | Feingold et al. |
| 6,406,494 | B1 | 6/2002 | Laguette et al. |
| 6,410,643 | B1 | 6/2002 | Swanson |
| 6,436,092 | B1 | 8/2002 | Peyman |
| 6,443,985 | B1 | 9/2002 | Woods |
| 6,464,724 | B1 | 10/2002 | Lynch et al. |
| 6,464,725 | B2 | 10/2002 | Skotton |
| 6,471,666 | B1 | 10/2002 | Odrich |
| 6,488,708 | B2 | 12/2002 | Sarfarazi |
| 6,491,697 | B1 | 12/2002 | Clark et al. |
| 6,493,151 | B2 | 12/2002 | Schachar |
| 6,497,708 | B1 | 12/2002 | Cumming |
| 6,503,275 | B1 | 1/2003 | Cumming |
| 6,508,779 | B1 | 1/2003 | Suson |
| 6,508,803 | B1 | 1/2003 | Horikawa et al. |
| 6,510,600 | B2 | 1/2003 | Yaron et al. |
| 6,517,523 | B1 | 2/2003 | Kaneko et al. |
| 6,517,577 | B1 | 2/2003 | Callahan et al. |
| 6,528,602 | B1 | 3/2003 | Freeman et al. |
| 6,533,768 | B1 | 3/2003 | Hill |
| 6,537,283 | B2 | 3/2003 | Van Noy |
| 6,552,860 | B1 | 4/2003 | Alden |
| 6,585,768 | B2 | 7/2003 | Hamano et al. |
| 6,599,317 | B1 | 7/2003 | Weinschenk et al. |
| 6,601,956 | B1 | 8/2003 | Jean et al. |
| 6,605,093 | B1 | 8/2003 | Blake |
| 6,610,350 | B2 | 8/2003 | Suzuki et al. |
| 6,616,691 | B1 | 9/2003 | Tran |
| 6,616,692 | B1 | 9/2003 | Glick et al. |
| 6,626,858 | B2 | 9/2003 | Lynch et al. |
| 6,638,239 | B1 | 10/2003 | Bergheim et al. |
| 6,638,306 | B2 | 10/2003 | Cumming |
| 6,645,245 | B1 | 11/2003 | Preussner |
| 6,660,035 | B1 | 12/2003 | Lang et al. |
| 6,676,607 | B2 | 1/2004 | De Juan et al. |
| 6,699,210 | B2 | 3/2004 | Williams et al. |
| 6,699,211 | B2 | 3/2004 | Savage |
| 6,709,108 | B2 | 3/2004 | Levine et al. |
| 6,712,848 | B1 | 3/2004 | Wolf et al. |
| 6,730,056 | B1 | 5/2004 | Ghaem et al. |
| 6,730,123 | B1 | 5/2004 | Klopotek |
| 6,783,544 | B2 | 8/2004 | Lynch et al. |
| 6,786,888 | B1 | 9/2004 | Zadno-Azizi et al. |
| 6,818,158 | B2 | 11/2004 | Pham et al. |
| 6,827,699 | B2 | 12/2004 | Lynch et al. |
| 6,827,738 | B2 | 12/2004 | Willis et al. |
| 6,836,374 | B2 | 12/2004 | Esch et al. |
| 6,860,601 | B2 | 3/2005 | Shadduck |
| 6,881,198 | B2 | 4/2005 | Brown |
| 6,881,225 | B2 | 4/2005 | Okada |
| 6,914,247 | B2 | 7/2005 | Duggan et al. |
| 6,923,815 | B2 | 8/2005 | Brady et al. |
| 6,926,736 | B2 | 8/2005 | Peng et al. |
| 6,939,298 | B2 | 9/2005 | Brown et al. |
| 6,949,093 | B1 | 9/2005 | Peyman |
| 6,966,649 | B2 | 11/2005 | Shadduck |
| 6,969,384 | B2 | 11/2005 | De Juan et al. |
| 6,969,403 | B2 | 11/2005 | Peng et al. |
| 6,981,958 | B1 | 1/2006 | Gharib et al. |
| 7,001,374 | B2 | 2/2006 | Peyman |
| 7,060,094 | B2 | 6/2006 | Shahinpoor et al. |
| 7,070,276 | B2 | 7/2006 | Koretz |
| 7,147,650 | B2 | 12/2006 | Lee |
| 7,156,854 | B2 | 1/2007 | Brown et al. |
| 7,264,351 | B2 | 9/2007 | Shadduck |
| 7,297,130 | B2 | 11/2007 | Bergheim et al. |
| 7,311,194 | B2 | 12/2007 | Jin et al. |
| 7,331,984 | B2 | 2/2008 | Tu et al. |
| 7,429,263 | B2 | 9/2008 | Vaquero et al. |
| 7,438,723 | B2 | 10/2008 | Esch |
| 7,615,073 | B2 | 11/2009 | Deacon et al. |
| 7,637,947 | B2 | 12/2009 | Smith et al. |
| 7,850,638 | B2 | 12/2010 | Theodore Coroneo |
| 7,867,186 | B2 | 1/2011 | Haffner et al. |
| 7,867,205 | B2 | 1/2011 | Bergheim et al. |
| 7,931,596 | B2 | 4/2011 | Rachlin et al. |
| 7,988,290 | B2 | 8/2011 | Campbell et al. |
| 8,012,115 | B2 | 9/2011 | Karageozian |
| 8,034,105 | B2 | 10/2011 | Stegmann et al. |
| 8,052,752 | B2 | 11/2011 | Woods et al. |
| 8,246,631 | B2 | 8/2012 | Pynson |
| 8,308,701 | B2 | 11/2012 | Horvath et al. |
| 8,314,927 | B2 | 11/2012 | Choi et al. |
| 8,382,769 | B2 | 2/2013 | Inoue |
| 8,447,086 | B2 | 5/2013 | Hildebrand et al. |
| 8,480,734 | B2 | 7/2013 | Kellan et al. |
| 8,486,128 | B2 | 7/2013 | Jen et al. |
| 8,523,941 | B2 | 9/2013 | Ichinohe et al. |
| 8,540,659 | B2 | 9/2013 | Berlin |
| 8,551,166 | B2 | 10/2013 | Schieber et al. |
| 8,613,766 | B2 | 12/2013 | Richardson et al. |
| 8,641,748 | B2 | 2/2014 | Hebert et al. |
| 8,647,659 | B2 | 2/2014 | Robinson et al. |
| 8,657,776 | B2 | 2/2014 | Wardle et al. |
| 8,702,727 | B1 | 4/2014 | Harrington et al. |
| 8,758,361 | B2 | 6/2014 | Kobayashi et al. |
| 8,814,819 | B2 | 8/2014 | De Juan et al. |
| 8,888,845 | B2 | 11/2014 | Vaquero et al. |
| 8,900,298 | B2 | 12/2014 | Anvar et al. |
| 8,961,447 | B2 | 2/2015 | Schieber et al. |
| 8,974,511 | B2 | 3/2015 | Horvath et al. |
| 8,992,609 | B2 | 3/2015 | Shadduck |
| 9,039,650 | B2 | 5/2015 | Schieber et al. |
| 9,155,655 | B2 | 10/2015 | Schieber et al. |
| 9,155,656 | B2 | 10/2015 | Schaller et al. |

(56) References Cited

U.S. PATENT DOCUMENTS

| | | |
|---|---|---|
| 9,277,987 B2 | 3/2016 | Smiley et al. |
| 9,326,846 B2 | 5/2016 | Devita Gerardi et al. |
| 9,329,306 B2 | 5/2016 | Huang et al. |
| 9,351,874 B2 | 5/2016 | Schieber et al. |
| 9,358,156 B2 | 6/2016 | Wardle et al. |
| 9,402,767 B2 | 8/2016 | Schieber et al. |
| 9,579,234 B2 | 2/2017 | Wardle et al. |
| 9,603,741 B2 | 3/2017 | Berlin |
| 9,610,155 B2 | 4/2017 | Matthews |
| 9,642,746 B2 | 5/2017 | Berlin |
| 9,693,901 B2 | 7/2017 | Horvath et al. |
| 9,693,902 B2 | 7/2017 | Euteneuer et al. |
| 9,730,638 B2 | 8/2017 | Haffner et al. |
| 9,795,473 B2 | 10/2017 | Smiley et al. |
| 9,872,762 B2 | 1/2018 | Scholl et al. |
| 9,872,763 B2 | 1/2018 | Smiley et al. |
| 10,042,183 B2 | 8/2018 | Goodenough et al. |
| 10,159,566 B2 | 12/2018 | Hadba et al. |
| 10,195,020 B2 | 2/2019 | Matthews |
| 10,299,913 B2 | 5/2019 | Smiley et al. |
| 10,335,314 B2 | 7/2019 | Berlin |
| 10,357,356 B2 | 7/2019 | Smiley et al. |
| 10,363,168 B2 | 7/2019 | Schieber et al. |
| 10,492,949 B2 | 12/2019 | Wardle et al. |
| 10,534,113 B2 | 1/2020 | Shadduck |
| 10,617,558 B2 | 4/2020 | Schieber et al. |
| 2001/0001836 A1 | 5/2001 | Cumming |
| 2001/0021835 A1 | 9/2001 | Mitchell et al. |
| 2001/0039449 A1 | 11/2001 | Johnson et al. |
| 2002/0003546 A1 | 1/2002 | Mochimaru et al. |
| 2002/0013546 A1 | 1/2002 | Grieshaber et al. |
| 2002/0013553 A1 | 1/2002 | Pajunk et al. |
| 2002/0055776 A1 | 5/2002 | Juan et al. |
| 2002/0072673 A1 | 6/2002 | Yamamoto et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0133167 A1 | 9/2002 | Harish et al. |
| 2002/0133168 A1 | 9/2002 | Smedley et al. |
| 2002/0133228 A1 | 9/2002 | Sarver |
| 2002/0161434 A1 | 10/2002 | Laguette et al. |
| 2002/0165522 A1 | 11/2002 | Holmen |
| 2002/0169130 A1 | 11/2002 | Tu et al. |
| 2002/0177896 A1 | 11/2002 | Israel |
| 2002/0193804 A1 | 12/2002 | Tickle |
| 2002/0193805 A1 | 12/2002 | Ott et al. |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0014092 A1 | 1/2003 | Neuhann |
| 2003/0018384 A1 | 1/2003 | Valyunin et al. |
| 2003/0040754 A1 | 2/2003 | Mitchell et al. |
| 2003/0050696 A1 | 3/2003 | Cumming |
| 2003/0055372 A1 | 3/2003 | Lynch et al. |
| 2003/0060752 A1 | 3/2003 | Bergheim et al. |
| 2003/0060784 A1 | 3/2003 | Hilgers et al. |
| 2003/0060878 A1 | 3/2003 | Shadduck |
| 2003/0060881 A1 | 3/2003 | Glick et al. |
| 2003/0069637 A1 | 4/2003 | Lynch et al. |
| 2003/0078657 A1 | 4/2003 | Zadno-Azizi et al. |
| 2003/0083744 A1 | 5/2003 | Khoury |
| 2003/0109926 A1 | 6/2003 | Portney |
| 2003/0120200 A1 | 6/2003 | Bergheim |
| 2003/0125351 A1 | 7/2003 | Azuma et al. |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0180522 A1 | 9/2003 | DeSimone et al. |
| 2003/0181848 A1 | 9/2003 | Bergheim et al. |
| 2003/0183960 A1 | 10/2003 | Buazza et al. |
| 2003/0187384 A1 | 10/2003 | Bergheim |
| 2003/0199977 A1 | 10/2003 | Cumming |
| 2003/0229303 A1 | 12/2003 | Haffner et al. |
| 2003/0236375 A1 | 12/2003 | Salamone et al. |
| 2004/0001180 A1 | 1/2004 | Epstein |
| 2004/0006386 A1 | 1/2004 | Valint et al. |
| 2004/0015140 A1 | 1/2004 | Shields |
| 2004/0015236 A1 | 1/2004 | Sarfarazi |
| 2004/0024345 A1 | 2/2004 | Gharib et al. |
| 2004/0024453 A1 | 2/2004 | Castillejos |
| 2004/0059343 A1 | 3/2004 | Shearer et al. |
| 2004/0066489 A1 | 4/2004 | Benedikt et al. |
| 2004/0073156 A1 | 4/2004 | Brown |
| 2004/0082939 A1 | 4/2004 | Berlin |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088048 A1 | 5/2004 | Richter et al. |
| 2004/0088050 A1 | 5/2004 | Norrby et al. |
| 2004/0092856 A1 | 5/2004 | Dahan |
| 2004/0098124 A1 | 5/2004 | Freeman et al. |
| 2004/0106975 A1 | 6/2004 | Solovay et al. |
| 2004/0111152 A1 | 6/2004 | Kelman |
| 2004/0111153 A1 | 6/2004 | Woods et al. |
| 2004/0122380 A1 | 6/2004 | Utterberg |
| 2004/0127843 A1 | 7/2004 | Tu et al. |
| 2004/0127984 A1 | 7/2004 | Paul et al. |
| 2004/0147870 A1 | 7/2004 | Burns et al. |
| 2004/0181279 A1 | 9/2004 | Nun |
| 2004/0186868 A1 | 9/2004 | Kim |
| 2004/0210185 A1 | 10/2004 | Tu et al. |
| 2004/0225357 A1 | 11/2004 | Worst et al. |
| 2004/0228013 A1 | 11/2004 | Goldstein et al. |
| 2004/0230203 A1 | 11/2004 | Yaguchi |
| 2004/0249333 A1 | 12/2004 | Bergheim |
| 2004/0254520 A1 | 12/2004 | Porteous et al. |
| 2004/0254521 A1 | 12/2004 | Simon |
| 2004/0260227 A1 | 12/2004 | Lisk et al. |
| 2004/0267359 A1 | 12/2004 | Makker et al. |
| 2005/0008673 A1 | 1/2005 | Snyder et al. |
| 2005/0021139 A1 | 1/2005 | Shadduck |
| 2005/0033308 A1 | 2/2005 | Callahan et al. |
| 2005/0038334 A1 | 2/2005 | Lynch et al. |
| 2005/0041200 A1 | 2/2005 | Rich |
| 2005/0049578 A1 | 3/2005 | Tu et al. |
| 2005/0060016 A1 | 3/2005 | Wu et al. |
| 2005/0080484 A1 | 4/2005 | Marmo et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0113911 A1 | 5/2005 | Peyman |
| 2005/0125003 A1 | 6/2005 | Pinchuk et al. |
| 2005/0125056 A1 | 6/2005 | Deacon et al. |
| 2005/0143750 A1 | 6/2005 | Vaquero |
| 2005/0146685 A1 | 7/2005 | Hanaki et al. |
| 2005/0147735 A1 | 7/2005 | Lowery et al. |
| 2005/0149183 A1 | 7/2005 | Shadduck |
| 2005/0171507 A1 | 8/2005 | Christian et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim |
| 2005/0209555 A1 | 9/2005 | Middleton et al. |
| 2005/0222577 A1 | 10/2005 | Vaquero |
| 2005/0222579 A1 | 10/2005 | Vaquero et al. |
| 2005/0240168 A1 | 10/2005 | Neuberger et al. |
| 2005/0244464 A1 | 11/2005 | Hughes |
| 2005/0245916 A1 | 11/2005 | Connor |
| 2005/0251253 A1 | 11/2005 | Gross |
| 2005/0251254 A1 | 11/2005 | Brady et al. |
| 2005/0255231 A1 | 11/2005 | Hill et al. |
| 2005/0260186 A1 | 11/2005 | Bookbinder et al. |
| 2005/0266047 A1 | 12/2005 | Tu et al. |
| 2005/0283162 A1 | 12/2005 | Stratas |
| 2005/0288619 A1 | 12/2005 | Gharib et al. |
| 2006/0061729 A1 | 3/2006 | Shadduck |
| 2006/0079828 A1 | 4/2006 | Brown |
| 2006/0084907 A1 | 4/2006 | Bergheim |
| 2006/0100701 A1 | 5/2006 | Esch et al. |
| 2006/0106370 A1 | 5/2006 | Baerveldt et al. |
| 2006/0110428 A1 | 5/2006 | Dejuan et al. |

(56) References Cited

U.S. PATENT DOCUMENTS

| | | |
|---|---|---|
| 2006/0116626 A1 | 6/2006 | Smedley et al. |
| 2006/0129129 A1 | 6/2006 | Smith |
| 2006/0129141 A1 | 6/2006 | Lin |
| 2006/0135642 A1 | 6/2006 | Makker et al. |
| 2006/0154981 A1 | 7/2006 | Klimko et al. |
| 2006/0155265 A1 | 7/2006 | Juhasz et al. |
| 2006/0158611 A1 | 7/2006 | Piers et al. |
| 2006/0178674 A1 | 8/2006 | Mcintyre |
| 2006/0189915 A1 | 8/2006 | Camras et al. |
| 2006/0189917 A1 | 8/2006 | Mayr et al. |
| 2006/0195187 A1 | 8/2006 | Stegmann et al. |
| 2006/0253196 A1 | 11/2006 | Woods |
| 2006/0276759 A1 | 12/2006 | Kinast et al. |
| 2007/0004886 A1 | 1/2007 | Schorzman et al. |
| 2007/0010880 A1 | 1/2007 | Esch |
| 2007/0027452 A1 | 2/2007 | Varner et al. |
| 2007/0121120 A1 | 5/2007 | Schachar |
| 2007/0129717 A1 | 6/2007 | Brown et al. |
| 2007/0191863 A1 | 8/2007 | De Juan et al. |
| 2007/0203578 A1 | 8/2007 | Scholl et al. |
| 2007/0213817 A1 | 9/2007 | Esch et al. |
| 2007/0219509 A1 | 9/2007 | Tashiro et al. |
| 2007/0260157 A1 | 11/2007 | Norrby |
| 2007/0276315 A1 | 11/2007 | Haffner et al. |
| 2007/0282245 A1 | 12/2007 | Tu et al. |
| 2007/0282438 A1 | 12/2007 | Hong et al. |
| 2007/0293872 A1 | 12/2007 | Peyman |
| 2007/0298068 A1 | 12/2007 | Badawi et al. |
| 2007/0299487 A1 | 12/2007 | Shadduck |
| 2008/0004699 A1 | 1/2008 | Ben Nun |
| 2008/0015488 A1 | 1/2008 | Tu et al. |
| 2008/0027460 A1 | 1/2008 | Kobayashi |
| 2008/0027537 A1 | 1/2008 | Gerlach et al. |
| 2008/0045878 A1 | 2/2008 | Bergheim |
| 2008/0065096 A1 | 3/2008 | Kappelhof et al. |
| 2008/0119827 A1 | 5/2008 | Kurtz et al. |
| 2008/0119865 A1 | 5/2008 | Meunier et al. |
| 2008/0125862 A1 | 5/2008 | Blake |
| 2008/0139769 A1 | 6/2008 | Iwamoto et al. |
| 2008/0200860 A1 | 8/2008 | Tu et al. |
| 2008/0200982 A1 | 8/2008 | Your |
| 2008/0234624 A2 | 9/2008 | Bergheim et al. |
| 2008/0269887 A1 | 10/2008 | Cumming |
| 2008/0269987 A1 | 10/2008 | Barron et al. |
| 2008/0300680 A1 | 12/2008 | Joshua |
| 2008/0306587 A1 | 12/2008 | Your |
| 2008/0312661 A1 | 12/2008 | Downer et al. |
| 2009/0005852 A1 | 1/2009 | Gittings et al. |
| 2009/0005865 A1 | 1/2009 | Smiley et al. |
| 2009/0018512 A1 | 1/2009 | Charles |
| 2009/0030415 A1 | 1/2009 | Gogolewski |
| 2009/0030425 A1 | 1/2009 | Smiley et al. |
| 2009/0036819 A1 | 2/2009 | Tu et al. |
| 2009/0036840 A1 | 2/2009 | Viray et al. |
| 2009/0036898 A1 | 2/2009 | Ichinohe et al. |
| 2009/0043321 A1 | 2/2009 | Conston et al. |
| 2009/0079940 A1 | 3/2009 | Dai et al. |
| 2009/0082860 A1 | 3/2009 | Schieber et al. |
| 2009/0112313 A1 | 4/2009 | Mentak |
| 2009/0118718 A1 | 5/2009 | Raksi et al. |
| 2009/0124773 A1 | 5/2009 | Zhou et al. |
| 2009/0171366 A1 | 7/2009 | Tanaka |
| 2009/0204053 A1 | 8/2009 | Nissan et al. |
| 2009/0204123 A1 | 8/2009 | Downer |
| 2009/0227934 A1 | 9/2009 | Euteneuer et al. |
| 2009/0228101 A1 | 9/2009 | Zadno-Azizi |
| 2009/0234449 A1 | 9/2009 | De Juan et al. |
| 2009/0259126 A1 | 10/2009 | Saal et al. |
| 2009/0270876 A1 | 10/2009 | Hoffmann et al. |
| 2009/0281520 A1 | 11/2009 | Highley et al. |
| 2009/0292293 A1 | 11/2009 | Bogaert et al. |
| 2009/0306774 A1 | 12/2009 | Park |
| 2009/0312836 A1 | 12/2009 | Pinchuk et al. |
| 2009/0318933 A1 | 12/2009 | Anderson |
| 2010/0010416 A1 | 1/2010 | Juan et al. |
| 2010/0063588 A1 | 3/2010 | Park |
| 2010/0069522 A1 | 3/2010 | Linhardt et al. |
| 2010/0094412 A1 | 4/2010 | Wensrich |
| 2010/0130985 A1 | 5/2010 | Tanaka |
| 2010/0137981 A1 | 6/2010 | Silvestrini et al. |
| 2010/0173866 A1 | 7/2010 | Hee et al. |
| 2010/0179653 A1 | 7/2010 | Argento et al. |
| 2010/0191177 A1 | 7/2010 | Chang et al. |
| 2010/0262174 A1 | 10/2010 | Sretavan et al. |
| 2011/0028948 A1 | 2/2011 | Raksi et al. |
| 2011/0028950 A1 | 2/2011 | Raksi et al. |
| 2011/0028951 A1 | 2/2011 | Raksi et al. |
| 2011/0028953 A1 | 2/2011 | Raksi et al. |
| 2011/0028958 A1 | 2/2011 | Raksi et al. |
| 2011/0087149 A1 | 4/2011 | Theodore Coroneo |
| 2011/0118834 A1 | 5/2011 | Lo et al. |
| 2011/0224597 A1 | 9/2011 | Stegmann et al. |
| 2011/0282442 A1 | 11/2011 | Scholl et al. |
| 2011/0282443 A1 | 11/2011 | Smiley et al. |
| 2011/0313522 A1 | 12/2011 | Hayes |
| 2011/0313523 A1 | 12/2011 | Hayes |
| 2012/0035524 A1 | 2/2012 | Silvestrini |
| 2012/0221102 A1 | 8/2012 | Tanaka et al. |
| 2012/0226351 A1 | 9/2012 | Peyman |
| 2012/0302861 A1 | 11/2012 | Marshall et al. |
| 2012/0323159 A1 | 12/2012 | Wardle et al. |
| 2013/0053954 A1 | 2/2013 | Rao et al. |
| 2013/0103146 A1 | 4/2013 | Smiley et al. |
| 2013/0150959 A1 | 6/2013 | Schieber et al. |
| 2013/0231603 A1 | 9/2013 | Wardle et al. |
| 2013/0253437 A1 | 9/2013 | Badawi et al. |
| 2013/0253438 A1 | 9/2013 | Badawi et al. |
| 2013/0267887 A1 | 10/2013 | Kahook et al. |
| 2013/0281907 A1 | 10/2013 | Wardle et al. |
| 2013/0281908 A1 | 10/2013 | Schaller et al. |
| 2014/0107556 A1 | 4/2014 | Silvestrini et al. |
| 2014/0121584 A1 | 5/2014 | Wardle et al. |
| 2014/0214161 A1 | 7/2014 | Schieber et al. |
| 2014/0249625 A1 | 9/2014 | Shadduck |
| 2014/0257478 A1 | 9/2014 | Mccafferty |
| 2014/0330375 A1 | 11/2014 | Mccafferty |
| 2015/0022780 A1 | 1/2015 | John et al. |
| 2015/0038893 A1 | 2/2015 | Haffner et al. |
| 2015/0148836 A1 | 5/2015 | Heeren |
| 2015/0223984 A1 | 8/2015 | Schieber et al. |
| 2015/0257874 A1 | 9/2015 | Hildebrand et al. |
| 2015/0305939 A1 | 10/2015 | Vera et al. |
| 2016/0058553 A1 | 3/2016 | Salahieh et al. |
| 2016/0128826 A1 | 5/2016 | Silvestrini et al. |
| 2016/0184091 A1 | 6/2016 | Smiley et al. |
| 2016/0184092 A1 | 6/2016 | Smiley et al. |
| 2016/0262875 A1 | 9/2016 | Smith et al. |
| 2017/0020662 A1 | 1/2017 | Shadduck |
| 2017/0164831 A1 | 6/2017 | Choo et al. |
| 2017/0172794 A1 | 6/2017 | Varner et al. |
| 2017/0172799 A1 | 6/2017 | Horvath |
| 2017/0172800 A1 | 6/2017 | Romoda et al. |
| 2017/0202708 A1 | 7/2017 | Berlin |
| 2017/0258581 A1 | 9/2017 | Borja et al. |
| 2017/0348150 A1 | 12/2017 | Horvath et al. |
| 2018/0147051 A1 | 5/2018 | Scholl et al. |
| 2018/0256395 A1 | 9/2018 | Escaf et al. |
| 2018/0318066 A1 | 11/2018 | Campin et al. |
| 2018/0360655 A1 | 12/2018 | Berlin |
| 2018/0369017 A1 | 12/2018 | Schieber et al. |
| 2019/0076243 A1 | 3/2019 | Hadba et al. |
| 2019/0240004 A9 | 8/2019 | Smiley et al. |
| 2019/0269500 A1 | 9/2019 | De Juan et al. |
| 2019/0343679 A1 | 11/2019 | Wardle et al. |
| 2019/0361231 A1 | 11/2019 | Kurz |
| 2019/0374333 A1 | 12/2019 | Shadduck |
| 2020/0000577 A1 | 1/2020 | Smiley et al. |
| 2020/0085620 A1 | 3/2020 | Euteneuer et al. |
| 2020/0197221 A1 | 6/2020 | Schieber et al. |
| 2020/0246134 A1 | 8/2020 | Hajela et al. |

(56) References Cited

U.S. PATENT DOCUMENTS

| | | |
|---|---|---|
| 2020/0261266 A1 | 8/2020 | Bley et al. |
| 2023/0089016 A1 | 3/2023 | Noda et al. |

FOREIGN PATENT DOCUMENTS

| | | |
|---|---|---|
| CN | 1378440 | 11/2002 |
| CN | 1384727 | 12/2002 |
| CN | 101039635 | 9/2007 |
| CN | 101277659 | 10/2008 |
| CN | 102271622 | 12/2011 |
| CN | 202288610 | 7/2012 |
| EP | 0898972 | 3/1999 |
| EP | 1332731 | 8/2003 |
| EP | 1356791 | 10/2003 |
| EP | 1659991 | 5/2006 |
| EP | 2060243 | 5/2009 |
| EP | 2192934 | 6/2010 |
| EP | 2346441 | 7/2011 |
| FR | 2655841 | 6/1991 |
| FR | 2784575 | 12/2000 |
| JP | 07-044938 | 5/1995 |
| JP | 08-501715 | 2/1996 |
| JP | 08-224295 | 9/1996 |
| JP | 09-294754 | 11/1997 |
| JP | 10-206609 | 8/1998 |
| JP | 11-047168 | 2/1999 |
| JP | 11-056998 | 3/1999 |
| JP | 11-169391 | 6/1999 |
| JP | 11-276509 | 10/1999 |
| JP | 11-332903 | 12/1999 |
| JP | 2001-502592 | 2/2001 |
| JP | 2003-144387 | 5/2003 |
| JP | 2003-524503 | 8/2003 |
| JP | 2003-530978 | 10/2003 |
| JP | 2006-051358 | 2/2006 |
| JP | 2006-341094 | 12/2006 |
| JP | 2007-513715 | 5/2007 |
| JP | 2007-518447 | 7/2007 |
| JP | 2008-531069 | 8/2008 |
| JP | 2008-307394 | 12/2008 |
| JP | 2009-034451 | 2/2009 |
| JP | 2009-291399 | 12/2009 |
| JP | 2010-017459 | 1/2010 |
| SU | 1810052 | 4/1993 |
| WO | WO 1995/002378 | 1/1995 |
| WO | WO 1997/006751 | 2/1997 |
| WO | WO 2000/041650 | 7/2000 |
| WO | WO 2000/064655 | 11/2000 |
| WO | WO 2001/060286 | 8/2001 |
| WO | WO 2001/089435 | 11/2001 |
| WO | WO 2001/097742 | 12/2001 |
| WO | WO 2002/051338 | 7/2002 |
| WO | WO 2004/010895 | 2/2004 |
| WO | WO 2004/046768 | 6/2004 |
| WO | WO 2004/072689 | 8/2004 |
| WO | WO 2005/018504 | 3/2005 |
| WO | WO 2005/084588 | 9/2005 |
| WO | WO 2006/004707 | 1/2006 |
| WO | WO 2006/047383 | 5/2006 |
| WO | WO 2006/088440 | 8/2006 |
| WO | WO 2007/005529 | 1/2007 |
| WO | WO 2007/005692 | 1/2007 |
| WO | WO 2007/030095 | 3/2007 |
| WO | WO 2007/061688 | 5/2007 |
| WO | WO 2007/128423 | 11/2007 |
| WO | WO 2007/138564 | 12/2007 |
| WO | WO 2009/100322 | 8/2009 |
| WO | WO 2009/154455 | 12/2009 |
| WO | WO 2011/119334 | 9/2011 |
| WO | WO 2012/006186 | 1/2012 |
| WO | WO 2012/129419 | 9/2012 |
| WO | WO 2013/142323 | 9/2013 |
| WO | WO 2014/095611 | 6/2014 |
| WO | WO 2014/152017 | 9/2014 |

OTHER PUBLICATIONS

Baughman, "Avoiding the shrink," *Nature*, vol. 425, pp. 667, Oct. 16, 2003.

Conlisk, A. T. et al. "Mass Transfer and Flow in Electrically Charged Micro- and Nano-channels," *Analytical Chemistry*, vol. 74; iss. 9; pp. 2139-2150; May 2002.

Dubbelman et al. "The Thickness of the Aging Human Lens Obtained from Corrected Scheimpflug Images," *Optometry & Vision Science*; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

Gordon, "Applications of shape memory polyurethanes," *Proceedings of the First Intl Conf. on Shape Memory and Superelastic Tech.*, Asilomar Conference Center, Pacific Grove, CA, USA, pp. 115-120, Mar. 1994.

Gruber et al. "Exhaustive soxhlet extraction for the complete removal of residual compounds," *Journal of Biomedical Materials Research*, vol. 53; No. 5; pp. 445-448; Mar. 2000.

Jeon et al., "Shape memory and nanostructure in poly(norbornyl-POSS) copolymers," *Polymer International*, vol. 49, pp. 453-457, May 2000.

Kim et al., "Polyurethanes having shape memory effects," *Polymer*, vol. 37, No. 26, pp. 5781-5793, Dec. 1996.

Lakes et al., "Dramatically stiffer elastic composite materials due to negative stiffness phase?," *Journal of the Mechanics and Physics of Solids*, vol. 50, pp. 979-1009, May 2002.

Lakes et al., "Extreme damping in composite materials with negative-stiffness inclusions," *Nature*, vol. 410, pp. 565-567, Mar. 29, 2001.

Lakes et al., "Microbuckling instability in elastomeric cellular sollids," *J. Materials Science*, vol. 28, pp. 4667-4672, Jan. 1993.

Lakes, "A broader view of membranes," *Nature*, vol. 414, pp. 503-504, Nov. 29, 2001.

Lakes, "Deformations in extreme matter," *Science*; perspectives; vol. 288; No. 5473; pp. 1976-1977; Jun. 16, 2000.

Lakes, "Extreme damping in compliant composites with a negative-stiffness phase," *Philosophical Magazine Letters*, vol. 81, No. 2, pp. 95-100, Feb. 2001.

Lakes, "Extreme damping in composite materials with a negative stiffness phase," *Physical Review Letters*, vol. 86, No. 13, pp. 2897-2900, Mar. 26, 2001.

Lakes, "Negative poisson's ratio materials," *Science*, vol. 238, pp. 551, Oct. 23, 1987.

Lakes, "No. contractile obligations," *Nature*, vol. 358, pp. 713-714, Dec. 31, 1992.

Langenbucher et al., "Computerized calculation scheme for toric intraocular lenses," *Acta Ophthalmologica Scandinavica*, vol. 82, No. 3, pp. 270-276, Jun. 2004.

Lendlein et al., "Biodegradable, elastic shape-memory polymers for potential biomedical applications", *Science*; vol. 296; pp. 1673-1676; May 31, 2002.

Lendlein et al., "Shape-memory polymers," *Angew. Chem. Int. Ed.*; vol. 41; pp. 2034-2057; Jun. 2002.

Li et al., "Crystallinity and morphology of segmented polyurethanes with different soft-segment length," *Journal of Applied Polymer Science*, vol. 62, pp. 631-638, Oct. 1996.

Liu et al., "Thermomechanical characterization of a tailored series of shape memory polymers," *Journal of Applied Medical Polymers*, vol. 6, No. 2, Dec. 2002.

Mather et al., "Strain recovery in POSS hybrid thermoplastics," *Polymer Preprints*, vol. 41, No. 1, pp. 528-529, Feb. 2000.

Metcalfe et al., "Cold hibernated elastic memory foams for endovascular interventions," *Biomaterials*, vol. 24, pp. 491-497, Feb. 2003.

Qiao et al., Bio-inspired accommodating fluidic intraocular lens; *Optics Letters*; vol. 34; No. 20; pp. 3214-3216; Oct. 15, 2009.

Rosales et al., Pentacam Scheimpflug QuantitativeImaging of the Crystalline Lens andIntraocular Lens; J. Refractive Surgery; vol. 25; pp. 421-428; May 2009.

Takahashi et al., "Structure and properties of shape-memory polyurethane block copolymers," *Journal of Applied Polymer Science*, vol. 60, pp. 1061-1069, May 1996.

(56) References Cited

OTHER PUBLICATIONS

Tehrani et al. "Capsule measuring ring to predict capsular bag diameter and follow its course after foldable intraocular lens implantation," *J Cataract Refract Surg.*; vol. 29; No. 11; pp. 2127-2134; Nov. 29, 2003.

Tobushi et al., "Thermomechanical properties of shape memory polymers of polyurethane series and their applications," *Journal de Physique IV, Colloque C1*, vol. 6, pp. 377-384, Aug. 1996.

U.S. Appl. No. 16/268,280, filed Feb. 5, 2019 in the name of Matthews et al., Final Office Action mailed Oct. 2, 2020.

Vass et al. "Prediction of pseudophakic capsular bag diameter based on biometric variables," *J Cataract Refract Surg.*; vol. 25; pp. 1376-1381; Oct. 1999.

Wang et al., "Deformation of extreme viscoelastic metals and composites," *Materials Science and Enginerring A*, vol. 370, pp. 41-49, Apr. 15, 2004.

Wang et al., "Extreme stiffness systems due to negative stiffness elements," *American Journal of Physics*, vol. 72, No. 1, pp. 40-50, Jan. 2004.

Wang et al., "Stable extremely-high-damping discrete viscoelastic systems due to native stiffness elements," *Applied Physics Letters*, vol. 84, No. 22, pp. 4451-4453, May 31, 2004.

Wyant et al; "Basic Wavefront Aberration Theory for Optical Metrology," *Applied Optics and Optical Engineering*, vol. XI, pp. 1, 28-39, Aug. 10, 1992.

Xu et al., "Making negative poisson's ratio microstructures by soft lithography," *Advanced Materials*, vol. 11, No. 14, pp. 1186-1189, Jun. 1999.

U.S. Appl. No. 17/357,463, filed Jun. 24, 2021.
U.S. Appl. No. 16/268,280, filed Feb. 5, 2019.
U.S. Appl. No. 14/776,752, filed Sep. 15, 2015.

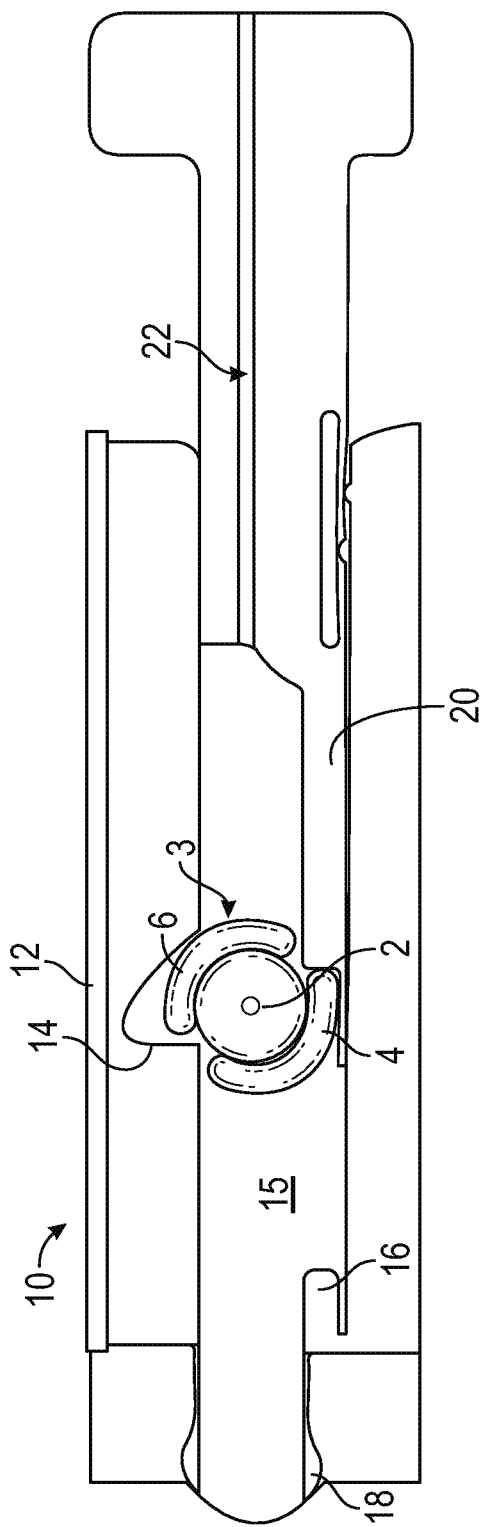
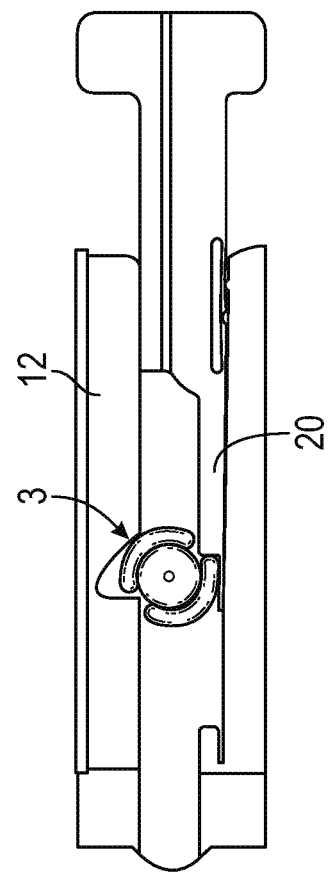
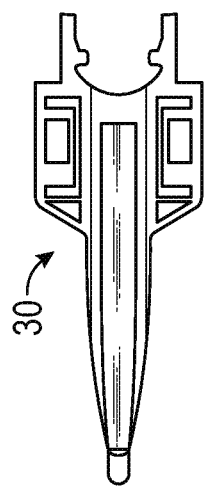
FIG. 1
FIG. 2

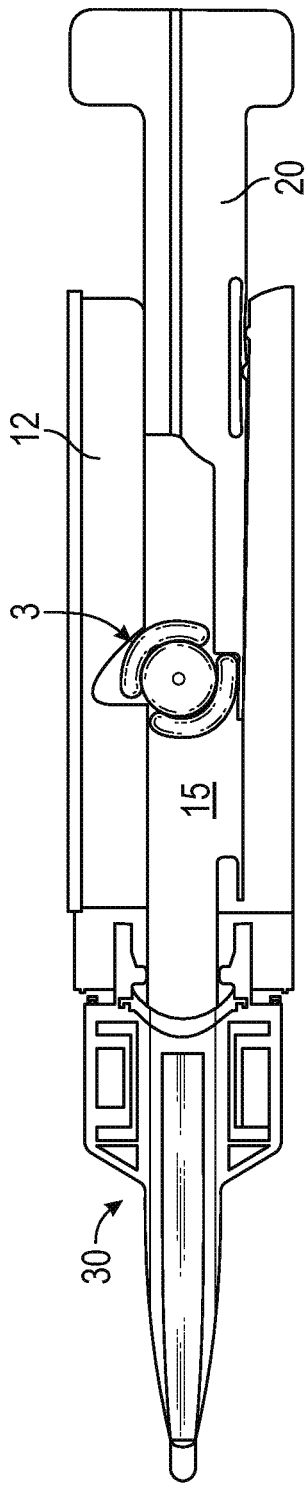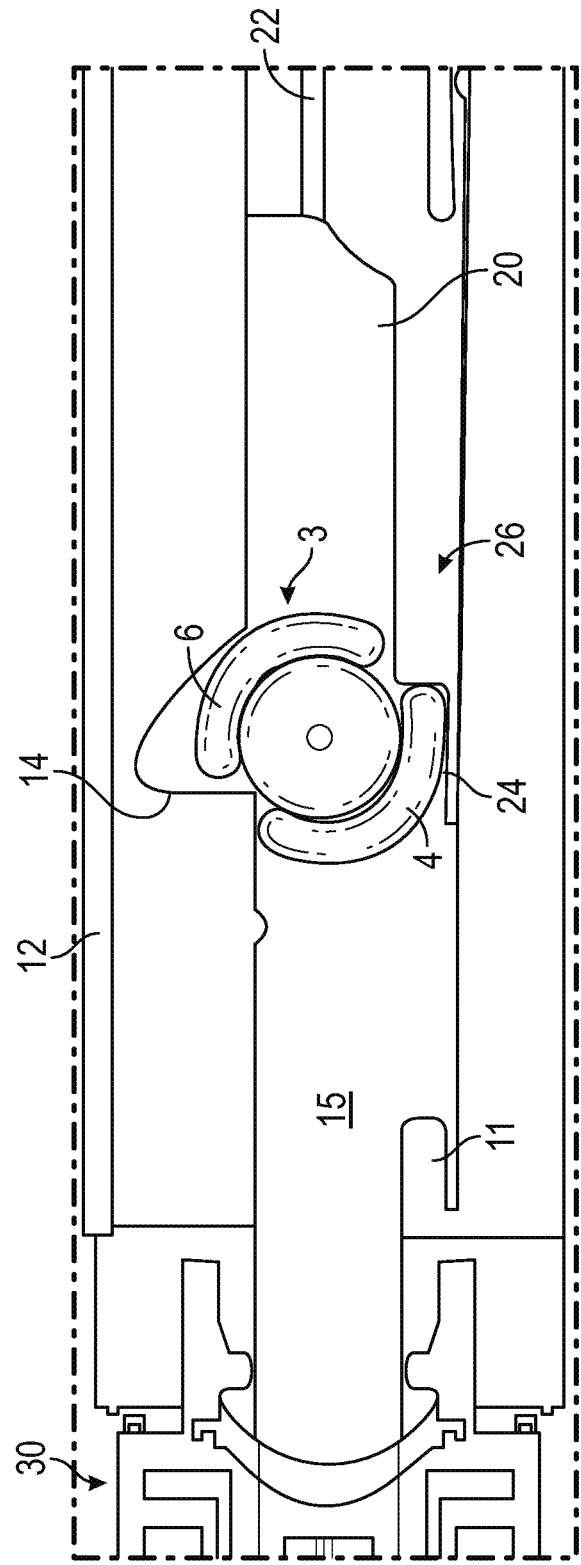
FIG. 3
FIG. 4

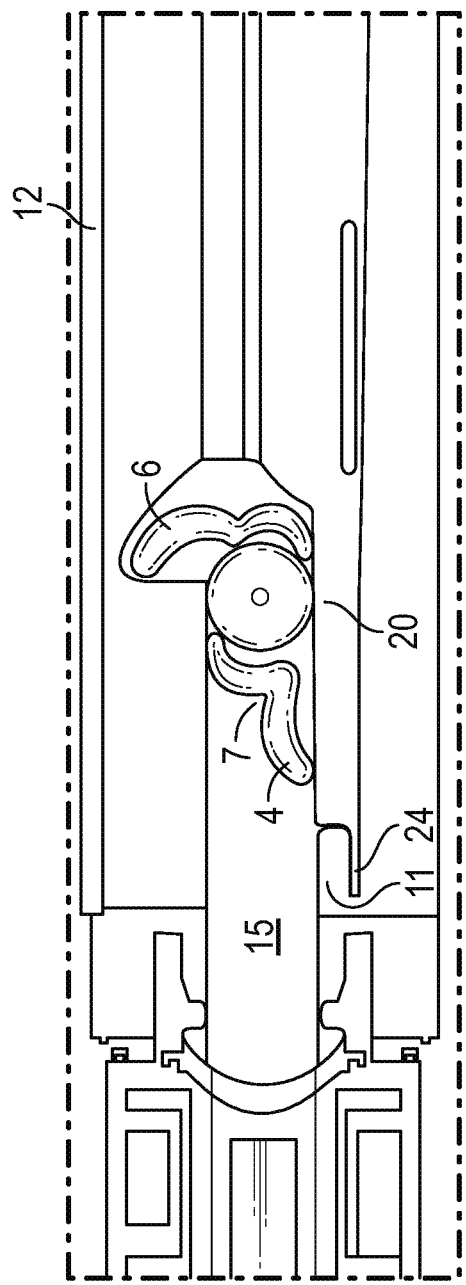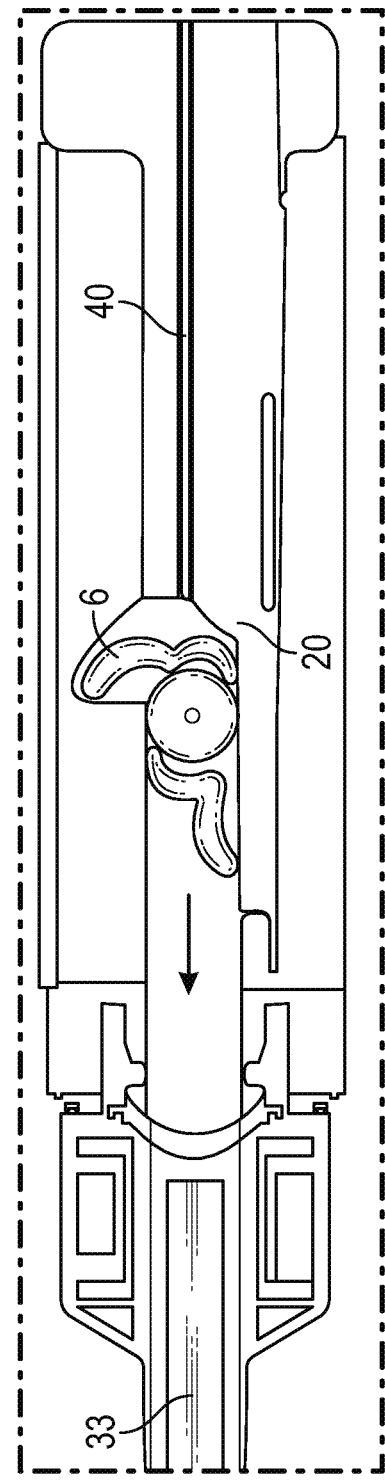
FIG. 7
FIG. 8

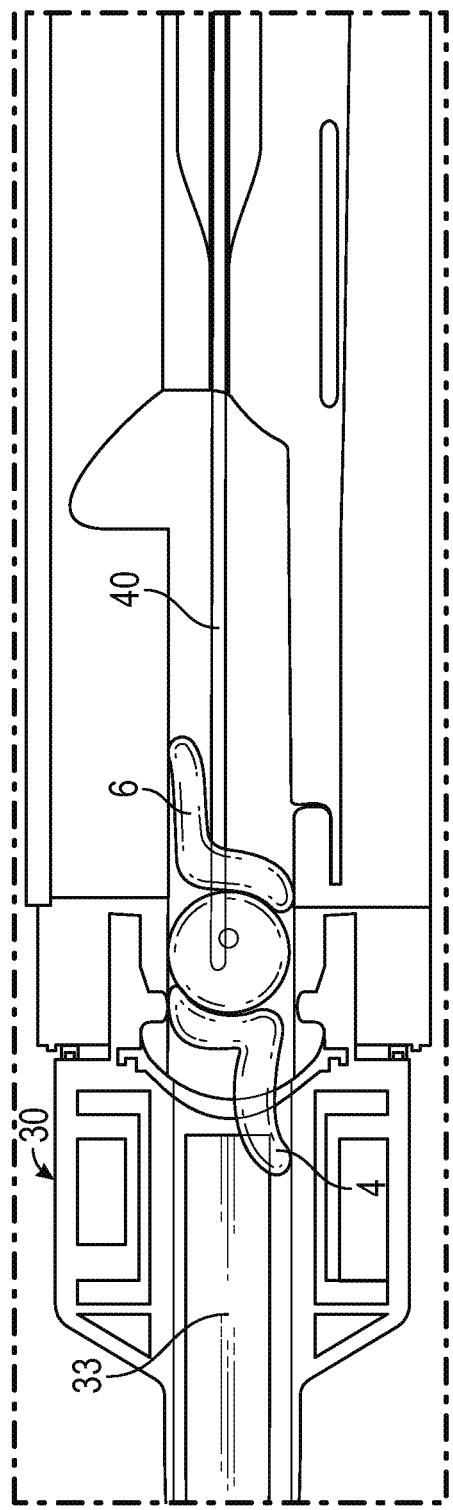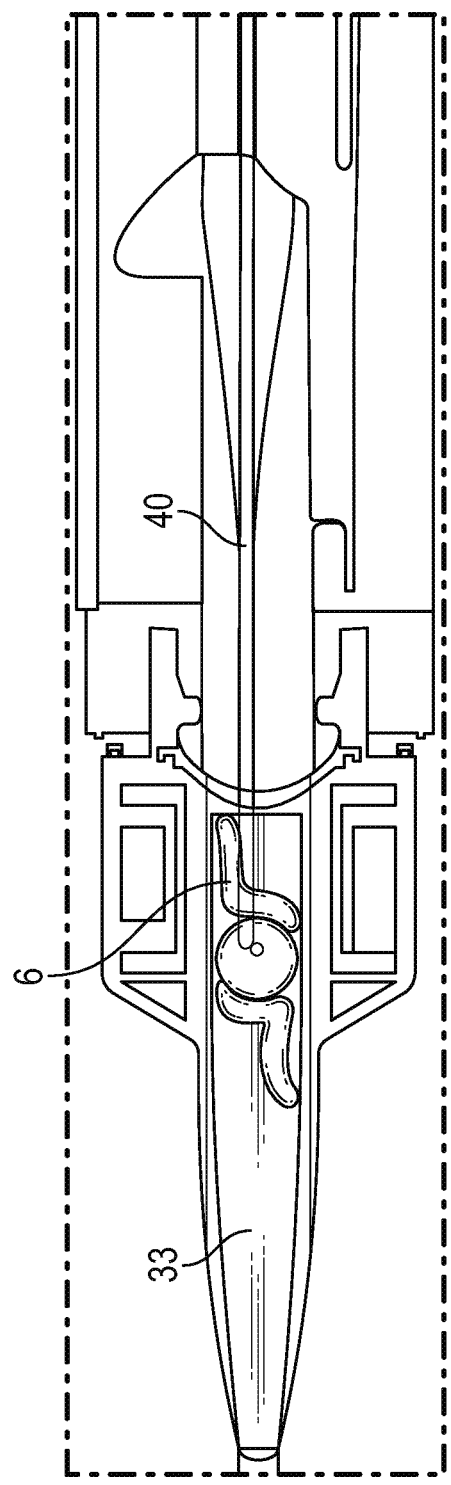

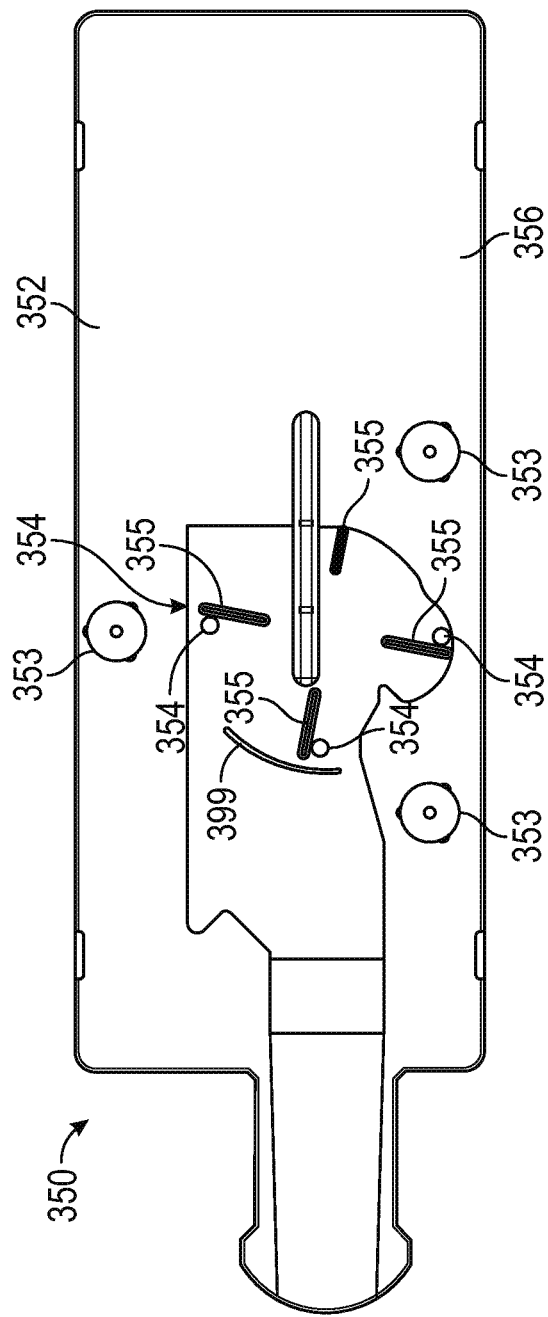
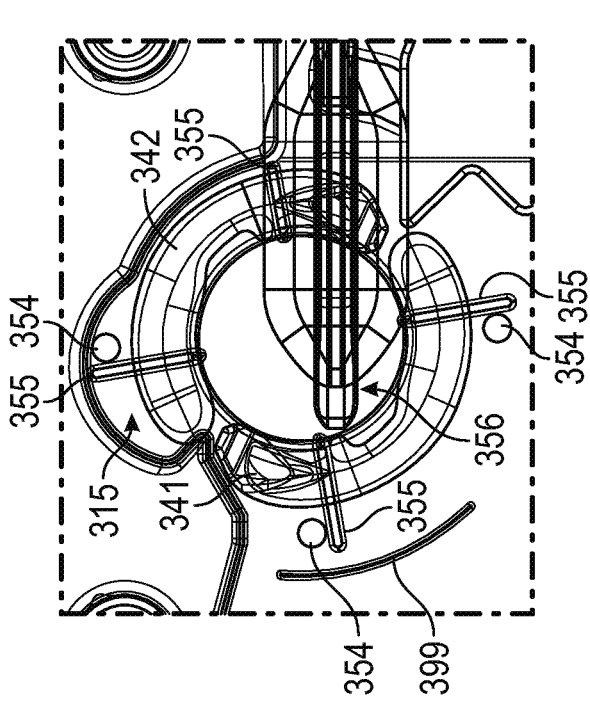

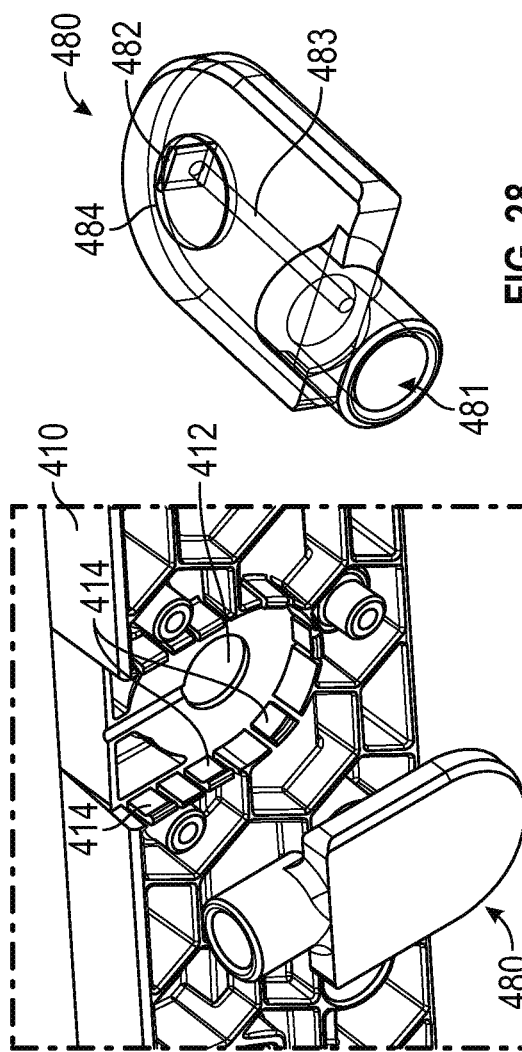
FIG. 27B
FIG. 28
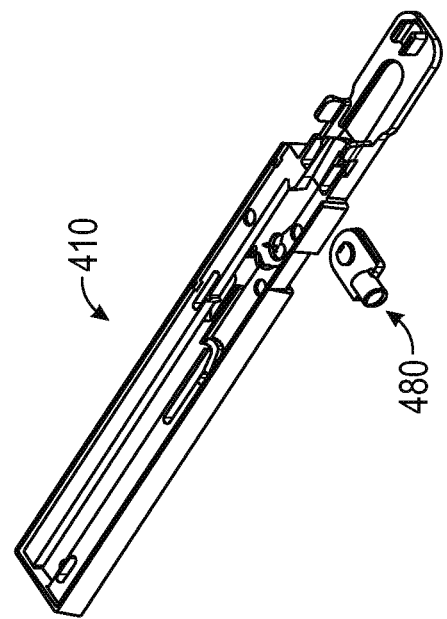
FIG. 27A
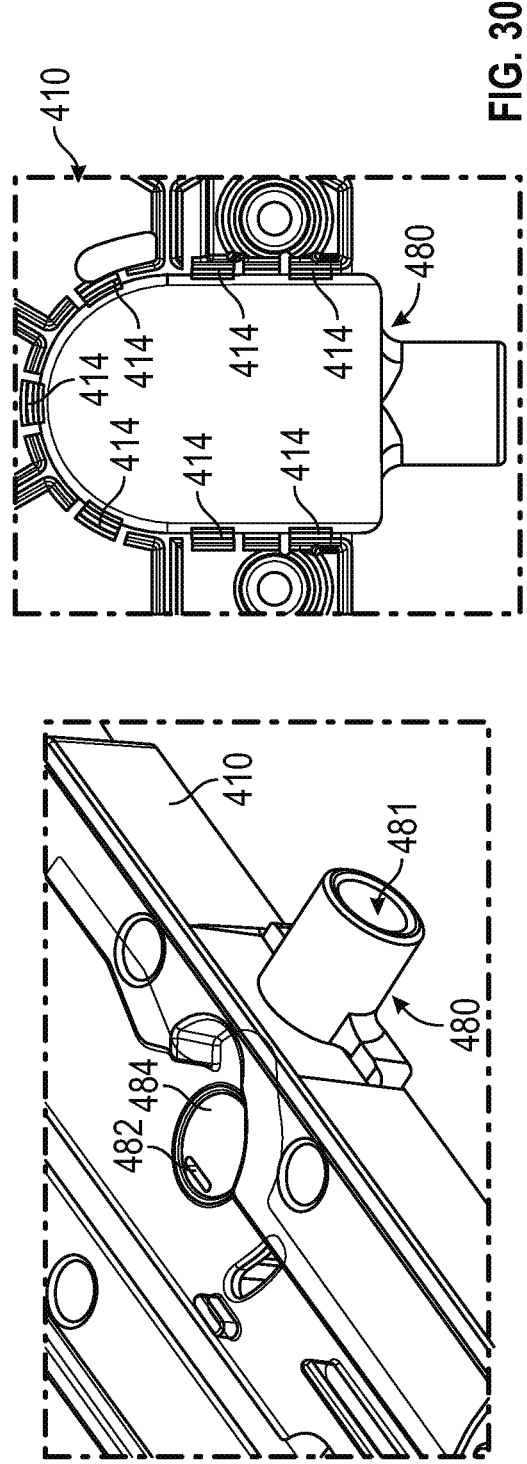
FIG. 30
FIG. 29

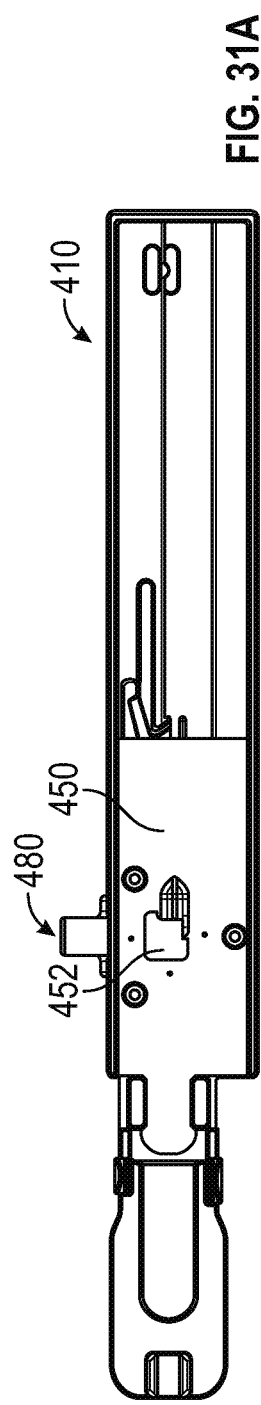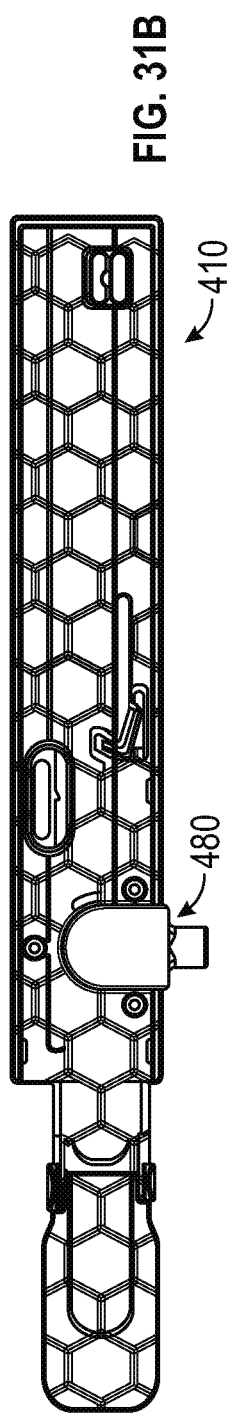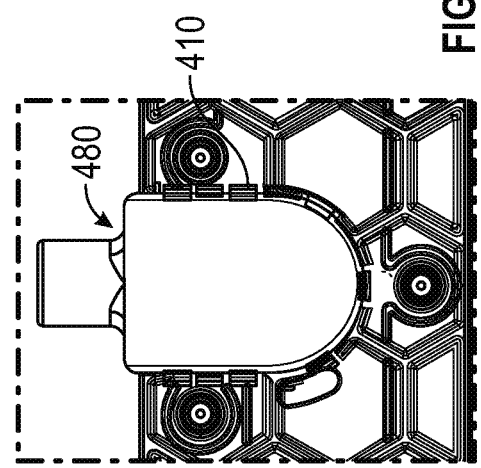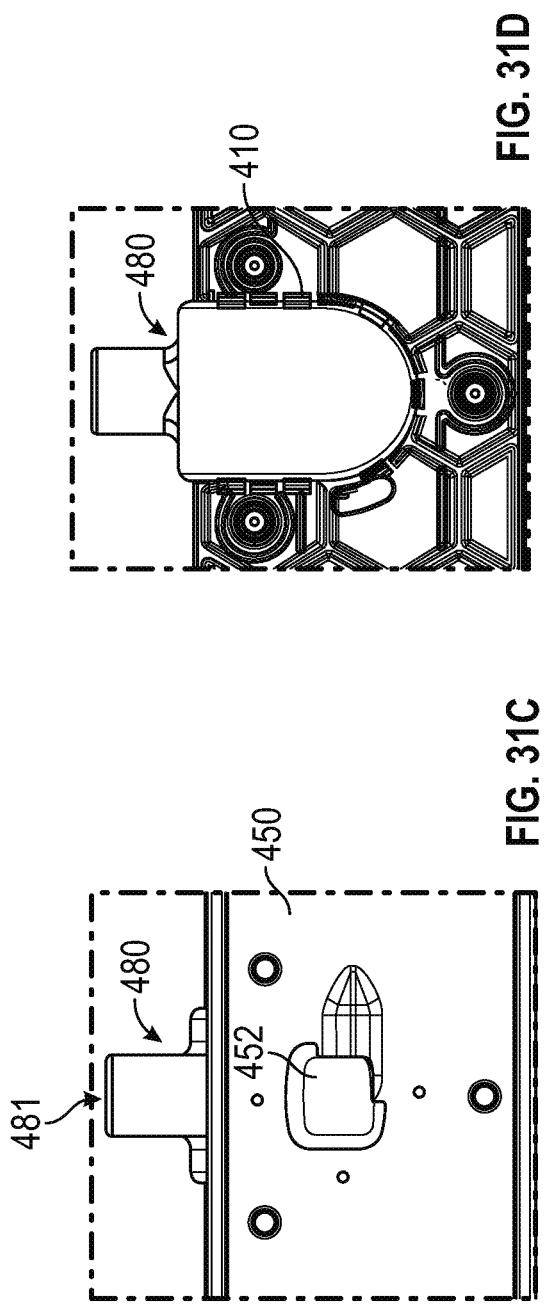

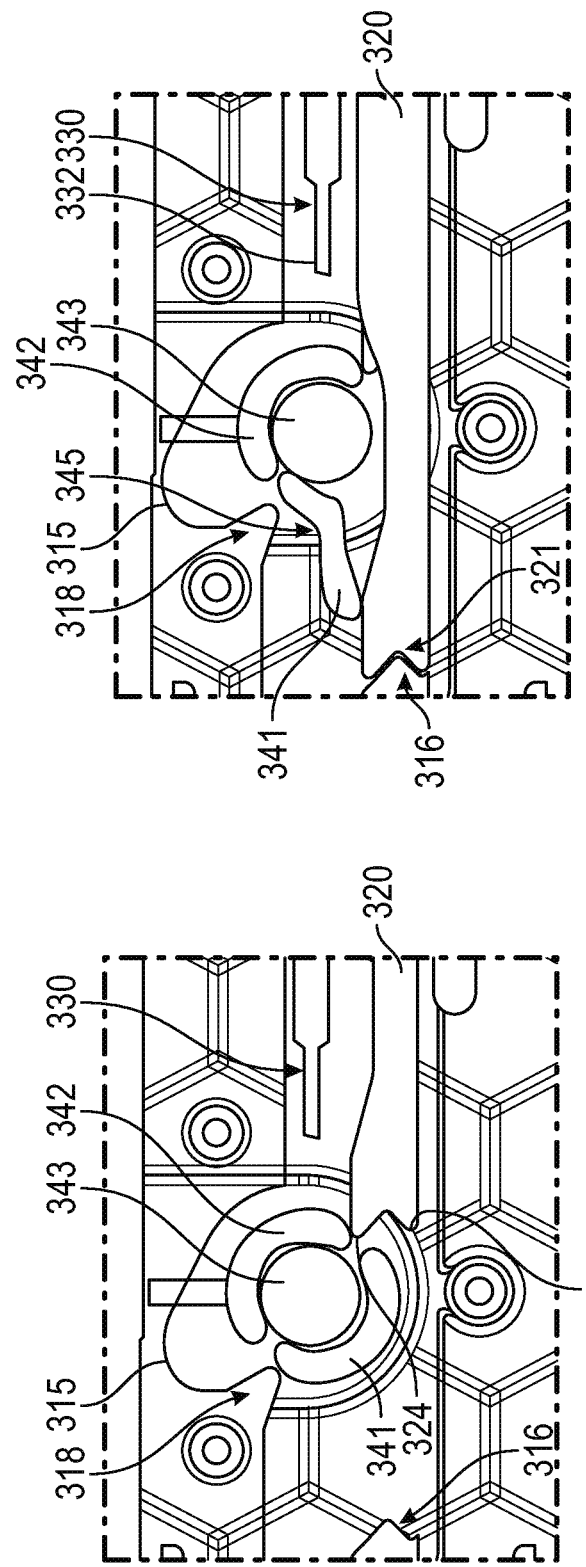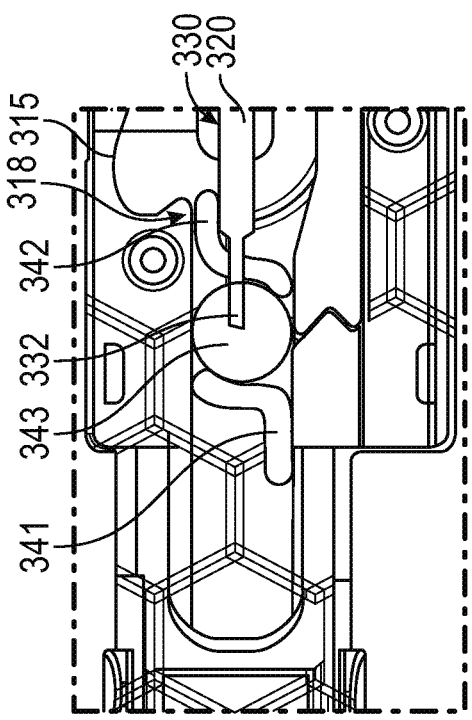

INTRAOCULAR LENS STORAGE AND LOADING DEVICES AND METHODS OF USE

CROSS REFERENCE TO RELATED APPLICATIONS

This application is a continuation of U.S. patent application Ser. No. 17/357,463 filed Jun. 24, 2021, which is a continuation of U.S. patent application Ser. No. 16/268,280 filed Feb. 5, 2019, now U.S. Pat. No. 11,071,622, which is a continuation of U.S. patent application Ser. No. 14/776,752 filed Sep. 15, 2015, now U.S. Pat. No. 10,195,020, which is a 371 application of PCT/US2014/030353 filed Mar. 17, 2014, which claims the benefit of U.S. Prov. Patent App. No. 61/799,755 filed Mar. 15, 2013, the disclosure of each is incorporated by reference herein.

This application is related to and incorporates by reference herein the disclosure of U.S. Pub. No. US 2014/0012277, published Jan. 9, 2014.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Procedures for loading and/or splaying haptics of an intraocular lens ("IOL") that use many individual tools or components, and involve manually displacing an IOL from an IOL carrier or other storage device into a delivery device or delivery lumen can be cumbersome and can risk damaging the IOL and delivery performance. An assembly that allows the user to quickly, reliably, and safely introduce an IOL into a delivery device or delivery lumen without manual manipulation or at least without risk of IOL damage would provide advantages over existing approaches.

SUMMARY OF THE DISCLOSURE

One aspect of the disclosure is a method of reconfiguring an intraocular lens haptic for delivery, comprising providing an intraocular lens in an intraocular lens receiving region of a base member such that a leading haptic is in a substantially at-rest configuration relative to an optic portion of the intraocular lens; moving a free end of the leading haptic away from the optic portion and towards a delivery lumen with an actuatable splaying member.

In some embodiments the substantially at-rest configuration is a curved configuration. The curved configuration can closely follow the curvature of an intraocular lens optic portion periphery.

In some embodiments the providing step comprises a trailing haptic in a substantially at-rest configuration relative to the optic portion of the intraocular lens.

In some embodiments the providing step comprises at least a portion of the leading haptic being positioned distally relative to a distal most portion of the optic portion.

In some embodiments moving the free end comprises moving the free end towards the delivery lumen without substantially moving a free end of a trailing haptic away from the optic portion.

In some embodiments moving the free end comprises moving the free end with an axially directed force from the splaying member.

In some embodiments moving the free end comprises engaging the free end with the actuatable splaying member.

In some embodiments moving the free end comprises distally moving the splaying member relative to the base member.

In some embodiments moving the free end comprises moving the free end from a position directly adjacent the optic periphery to a position further away from the optic periphery.

In some embodiments the providing step comprises the free end being closer to a first side of a base member channel than a second side of a base member channel, and the free end being accessible for direct engagement in the proximal direction.

In some embodiments moving the free end creates a bend in the leading haptic wherein a free end portion of the leading haptic extends away from an attached end portion of the leading haptic. Moving the free end can create a bend at a location in the leading haptic that is predisposed to bending when the free end is actuated with the splaying member.

In some embodiments the method further comprises moving a free end of a trailing haptic away from the optic portion. Moving the free end of the trailing haptic can comprise moving the free end of the trailing haptic in a proximal direction away from the leading haptic free end. Moving the free end of the trailing haptic can be moved upon a second actuation member.

In some embodiments the method further comprises loading the intraocular lens into the delivery lumen. The delivery lumen can be part of a separate delivery device. The delivery lumen can be integral with the base member. The delivery lumen can be part of the base member.

One aspect of the disclosure is a method of splaying leading and trailing haptics of an intraocular lens in preparation for delivery into an eye, comprising splaying a leading haptic relative to an optic portion of an intraocular lens with an actuatable splaying member; and splaying a trailing haptic relative to the optic portion, wherein splaying the leading haptic is initiated prior to initiating the splaying of the second haptic.

In some embodiments splaying the leading haptic is completed prior to initiating the splaying of the second haptic.

In some embodiments the method further comprises loading the intraocular lens into a delivery lumen.

In some embodiments splaying the trailing haptic occurs as a result of advancing the optic portion distally with an actuatable loading member, and wherein the actuatable loading member does not directly the free end of the trailing haptic.

One aspect of the disclosure is a method of splaying leading and trailing haptics of an intraocular lens in preparation for delivery into an eye, comprising actively splaying a leading haptic and passively splaying a trailing haptic. Actively splaying can comprise splaying the leading haptic free end by engaging and moving the leading haptic free end with an actuatable splaying member, and wherein passively splaying the trailing haptic occurs as a result of forces on the trailing haptic free end from a non-actuatable component. Actively splaying can comprise splaying the leading haptic free end by engaging and moving the leading haptic free end with an actuatable member, and wherein passively splaying the trailing haptic occurs as a result of a second actuatable member applying forces to a portion of the intraocular lens other than the free end of the trailing haptic.

One aspect of the disclosure is a method of positioning an intraocular lens in a base carrier, comprising: positioning an intraocular lens in an intraocular lens receiving area in a base member such that a leading haptic free end is closer to one side of a base member channel and is accessible for direct actuation in the proximal direction. The haptic free end can be facing proximally.

One aspect of the disclosure is a device for reconfiguring an intraocular lens in preparation for delivering the intraocular lens into an eye, comprising a base member comprising an intraocular lens receiving portion; a splaying member adapted to interact with the base member to engage and splay a leading haptic of an intraocular lens positioned in the lens receiving area; and a loading member adapted to interact with the base member to engage the intraocular lens after the leading haptic has been splayed and to advance the intraocular lens towards a delivery lumen.

In some embodiments the splaying member is configured to be axially movable relative to base member.

In some embodiments the splaying member interacts with the base member such that a distal end is not aligned with the center of the intraocular lens receiving area.

In some embodiments the splaying member interacts with the base member such that a distal end of the splaying member is disposed on a side of the lens receiving area.

In some embodiments the splaying member has branched distal end.

In some embodiments the base member has an element configured to mate with the branched distal end to prevent further distal movement.

In some embodiments the splaying member engages a first side wall of a base member channel and is slidable thereon.

In some embodiments the loading member is adapted to be axially movable relative to the base member.

In some embodiments the splaying member and the loading member are radially offset from one another in the base member. The base member can comprise a dividing element that maintains the relative positions of the splaying member and the loading member.

In some embodiments the loading member comprises a first extension extending distally from a top of a loading member body, and a second extension extending distally from the loading member body below the first extension, the first extension having a length greater than a length of the second extension.

In some embodiments the first extension extends distally and upwardly from the loading member body.

In some embodiments the first extension is adapted to flex where it extends upwardly from the loading member body. The loading member can interact with the base member such that as the loading member is advanced distally the first extension is disposed over a central region of the lens receiving area. The device can further comprise a lid adapted to be secured to the base member over the intraocular lens receiving area, the lid comprising a guide element adapted to engage with and cause the lowering of the first extension as the loading member is advanced distally.

In some embodiments the base member comprises a loading member lock out that prevents the loading member from being distally advanced until the lock out is moved, and wherein the splaying member comprises a release to move the lock out.

In some embodiments the base member comprises a trailing haptic receiving portion extending generally radially relative to the base member channel.

In some embodiments the device further comprises a lid comprising a plurality of posts configured to be disposed in a plurality of corresponding post guides in the base member. The lid can comprise a plurality of compression spokes extending downward from a bottom surface of the lid, the spokes adapted to engage with a leading haptic and a trailing haptic of the intraocular lens to lightly compress the haptics. In some embodiments at least two spokes engage each of the haptics.

BRIEF DESCRIPTION OF THE DRAWINGS

FIGS. 1-13 illustrate an intraocular lens loading process using an exemplary carrier in which leading and trailing haptics are splayed and the intraocular lens is loaded into a delivery lumen. The haptics are splayed in the delivery lumen.

FIG. 21 shows a bottom surface of an exemplary lid.

FIG. 22 illustrates an exemplary intraocular lens receiving area of a carrier, with an intraocular lens therein.

FIG. 27A shows a top exploded view of an exemplary carrier and bottom plug that incorporates a viscoelastic port.

FIG. 27B shows a bottom exploded close up view of an exemplary carrier and bottom plug that incorporates a viscoelastic port.

FIG. 28 illustrates an exemplary bottom plug that incorporates a viscoelastic port.

FIG. 29 is a top perspective assembled view showing a bottom plug secured to a carrier, showing fluid communication between a viscoelastic port and an intraocular lens receiving area.

FIG. 30 is a bottom view showing an exemplary bottom plus with viscoelastic port secured to a bottom of a carrier with a plurality of locks.

FIGS. 31A and 31B are top and bottom assembled views showing top and bottom plugs secured to a carrier, with the bottom plug having a viscoelastic port.

FIGS. 31C and 31D are close up views from FIGS. 31A and 31B.

FIGS. 32A-C illustrate an exemplary sequence of splaying leading and trailing haptics while loading an intraocular lens into a delivery lumen.

DETAILED DESCRIPTION

Figure 5:
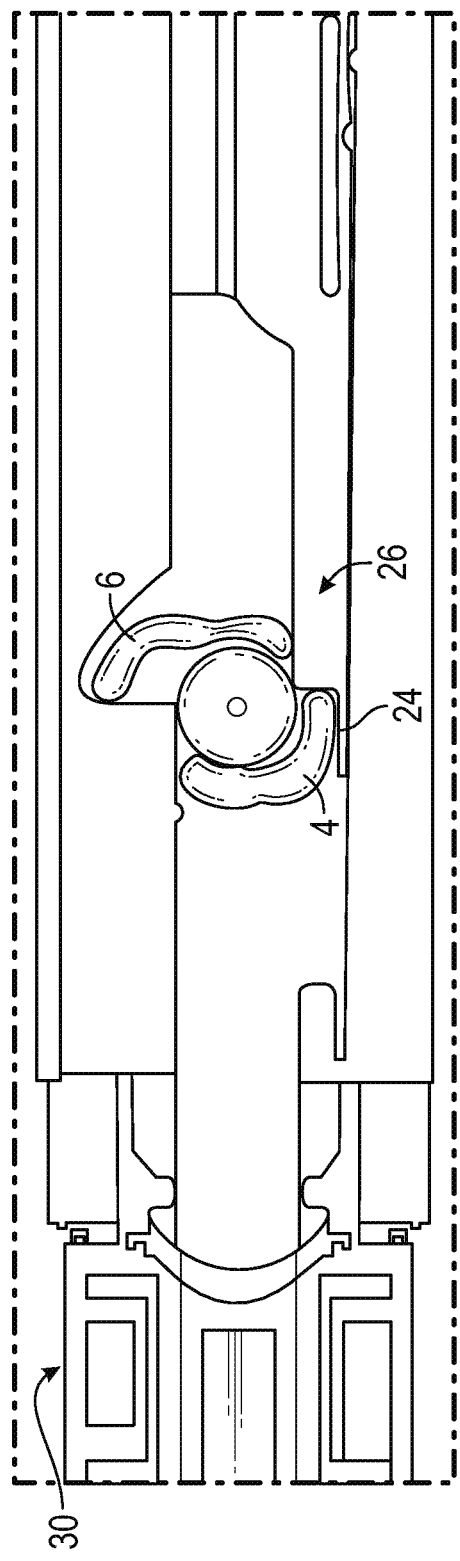

Some aspects of this disclosure describe storage devices for an intraocular lens. Some aspects of the disclosure describe devices and assemblies for loading an intraocular lens into a delivery device or delivery lumen. In some embodiments the devices and assemblies can be used for both storage and loading.

FIGS. 1-13 illustrate an exemplary embodiment of an IOL loading device, including a sequence of loading an exemplary intraocular lens into a delivery device. While FIGS. 1-13 are descried in the context of intraocular lens loading, the devices and assemblies in FIGS. 1-13 could also be used to store the intraocular lens. "Storage" as used herein includes any time the intraocular lens is kept in the device, and includes any sterilization procedures, shipping, and/or storage.

The loading devices herein are adapted to splay at least one haptic of the intraocular lens. The embodiment shown in FIGS. 1-13 illustrates a device adapted to splay two haptics of an intraocular lens, and is adapted to splay the two haptics sequentially. The term "splay" (or derivatives of "splay") as used herein refers to the act of re-orienting at least a portion of a haptic relative to an optic portion of an intraocular lens, such as from a substantial at-rest orientation in which the haptic has a generally curvilinear configuration to an orientation in which the haptic extends away from the optic. In the splayed orientation, at least a portion of the haptic does not follow the periphery of the optic portion, and extends away from the optic portion. In the splayed orientation a free end of the haptic is disposed further from the periphery of the optic than when the haptic is at an at-rest orientation relative to the optic. In the splayed orientation, at least a portion of the haptic has a more linear configuration than when the haptic is in the at-rest configuration.

The device(s) in FIGS. 1-13 are adapted to be used to load an IOL, such as the exemplary accommodating intraocular lens shown, into a delivery device or delivery lumen, from which the IOL is delivered into a patient's eye (such as into a capsular bag after the native capsule has been removed). A "delivery device" or "delivery lumen" as used herein may be referred to as a cartridge, and generally refers to a device or lumen that houses at least a portion of the intraocular lens for any period of time before the intraocular lens is implanted into the eye.

As an example, the loading devices and methods herein can be used to load an IOL into the cartridges described in U.S. application Ser. No. 13/835,876, filed Mar. 15, 2013, the disclosure of which is incorporated by reference herein. They can also be used to load an IOL into any suitable type of delivery device or delivery lumen.

The IOLs that can be loaded and splayed using devices and methods herein can be any type of IOL, such as accommodating, monofocal, and multifocal IOLs. FIGS. 1-13 illustrate the exemplary splaying of first and second haptics and the loading of a fluid-filled and fluid-driven accommodating IOL, exemplary details of which are described in U.S. application. Ser. No. 13/672,608, filed Nov. 8, 2012, while exemplary methods of delivering the IOL from the delivery device and into the eye are described in U.S. application Ser. No. 13/835,876, filed Mar. 15, 2013.

Procedures for loading and/or splaying of haptics that use many individual tools or components, and involve manually displacing an IOL from an IOL carrier or other storage device into a delivery device (e.g., cartridge) can be cumbersome and can risk damaging the lens and delivery performance. Preferable options include an assembly that allows the user to quickly, reliably, and safely introduce an IOL into a delivery device (e.g., a cartridge) without manual manipulation or at least without risk of IOL damage.

FIGS. 1-13 illustrate an exemplary splaying and loading lens carrier assembly that allows for safe transport of an accommodating IOL from manufacturing, through sterilization, storage, and into the operating environment. It does this with the lens in a substantially unstressed state to not alter power or shape of the lens through sterilization or storage. When ready for lens delivery, the loading IOL carrier can be mounted to a delivery device (e.g., a cartridge), which places the lens in a preferred state ready to deliver. The carriers herein are adapted to mate with cartridge and tray assemblies described in U.S. application Ser. No. 13/835,876, filed Mar. 15, 2013, such that the IOL can be loaded into those cartridges, but the disclosure is not so limited. The carrier assemblies herein can be used to load IOLs into other types of delivery devices.

As shown in the top view in FIG. 1, exemplary carrier 10 includes base 12, which acts as a tray to interface with other loading IOL carrier components as well as delivery system components (e.g., a cartridge). Base 12 also includes an IOL receiving region formed therein, and also acts as a guide for the IOL through the splay and loading process. The carrier assembly also includes a splay member 20. The splay member is adapted to move distally and proximally within a channel or guide in base 12 and functions to splay leading haptic 4 in a direction distal to optic 2 of IOL 3. The carrier assembly also includes loading member guide 22, which houses a loading member that moves distally to engage with and advance IOL 3 into cartridge 30 (or other delivery device or delivery lumen) and placing it at a predefined position in the cartridge to be ready for further assembly of a delivery device, such as the plungers described in U.S. application Ser. No. 13/835,876, filed Mar. 15, 2013. The carrier assembly also includes a carrier cover, or lid, not shown in FIGS. 1-13 for clarity. The cover retains the IOL, splay member, and loading member in the assembly. It also allows for viscoelastic lubricant to be introduced into the system without disrupting the lens orientation. It also allows for visualization of the loading procedure.

FIG. 1 illustrates IOL 3 within an IOL receiving region in base 12. Leading haptic 4 is disposed distally to optic 2, and trailing haptic 6 is generally proximal to optic 2. Splay member 20 is disposed within channel 15 in base 12. Splay member 20 has an extension on one side of the member 20 that, when the splay member 20 in advanced in channel 15, is adjacent a side wall of channel 15. In FIG. 1 the extension is shown on the bottom of splay member 20. The IOL is positioned within the receiving region, and the extension is disposed within base 12, such that the extension is positioned to engage with the free end of leading haptic 4 and initiate the splaying process as splaying member 20 is advanced distally.

FIG. 2 illustrates an exploded view with cartridge 30 separate from carrier base 12, but illustrating the end to which cartridge 30 is adapted to be secured to carrier base 12. FIG. 3 shows cartridge 30 secured to base 12.

Figure 15:
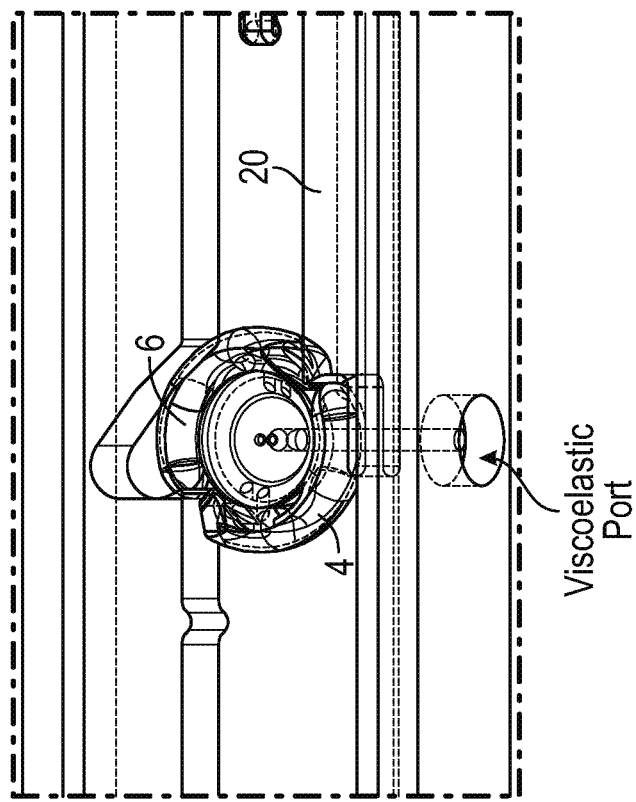
FIG. 15 illustrates an exemplary viscoelastic port adjacent to and in fluid communication with an intraocular lens receiving area in a carrier.

FIGS. 1-7 illustrate an exemplary method of splaying a leading haptic of the IOL within the carrier base. Prior to use, the loading IOL carrier can be sterilized and shipped with the IOL disposed therein (as shown in FIG. 1). Optionally the cartridge can be attached before sterilization, or the cartridge can be attached at the time of loading. Viscoelastic is introduced to the carrier through a port in the side of the loading IOL carrier that has a communicating port adjacent to lens, an example of which is shown in FIG. 15. Addition of viscoelastic lubricates the IOL, carrier, and cartridge components to allow for orientation and movement of the lens without sticking.

FIG. 1 illustrates the IOL within the carrier base such that the haptics are in an at-rest configuration and orientation, and are substantially unstressed. In the at-rest orientation, the haptics are both generally curvilinear, and extending around the periphery of optic 2. Trailing haptic 6 is oriented generally towards trailing haptic guide 14, which extends radially outward from channel 15. Both haptics closely follow the curvature of the optic portion, unlike some wire haptics, which extend further away from the optic portion and do not closely follow the curvature of the optic periphery. FIG. 3 illustrates the carrier mounted to cartridge 30. When the carrier is mounted to the cartridge, as shown in FIG. 3, the carrier channel 15 is in communication with a delivery lumen within the cartridge that is adapted to receive the IOL.

As can be seen in FIG. 1, splay member 20 includes an elongate distal portion extending from the proximal portion and is aligned with one side of the channel so that the distal end is positioned (and adapted) to engage and push the leading haptic distally when the splay slide is advanced. The IOL is oriented rotationally in FIG. 1 such that the elongate portion is adapted to push on the free end of the haptic (i.e., not the end of the haptic that is directly attached to optic 2). The free end is facing proximally and is accessible in the proximal direction.

Figure 6:
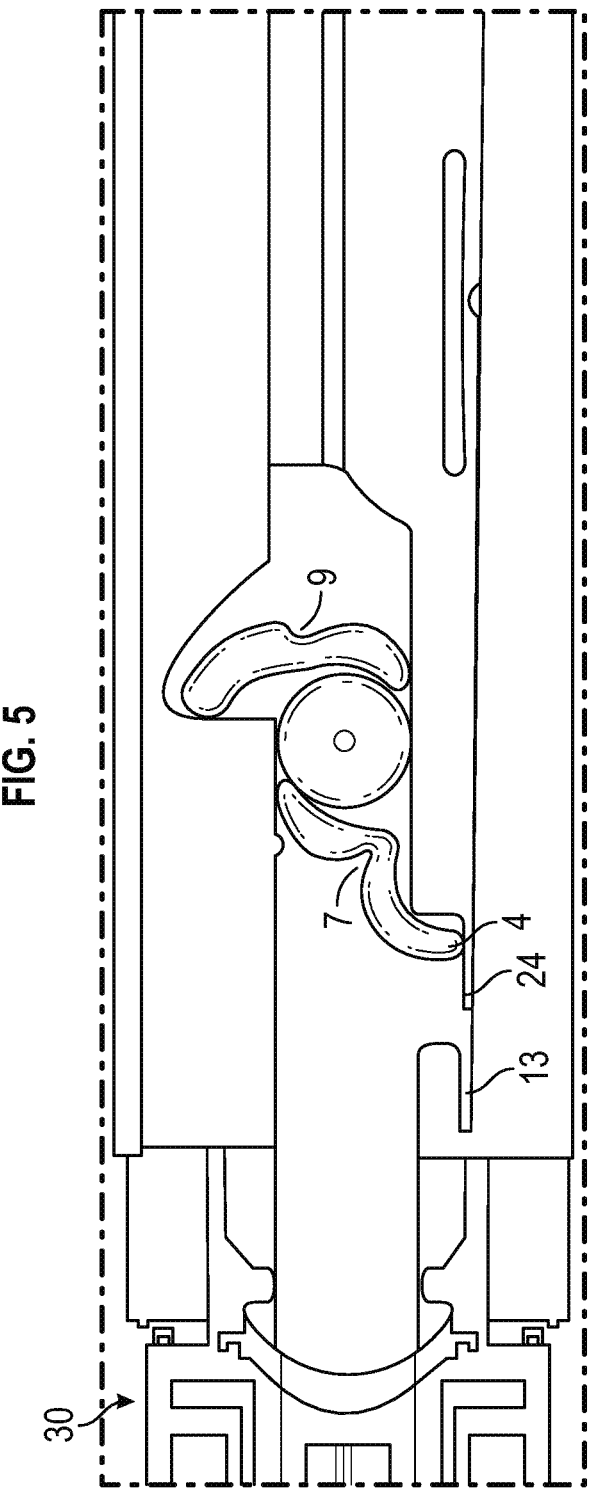

FIGS. 4-7 are top views of base 12 illustrating an exemplary sequence of splaying a leading haptic of an IOL. An operator actuates splay member 20 to advance it distally, causing splay member 20 to engage with the free end of leading haptic 4, as shown in FIG. 5. As splay member 20 continues to be advanced distally, the extending portion of splay member 20 pushes the free end of leading haptic 4 away from the periphery of optic 2, changing the configuration of the haptic and the haptic's orientation relative to optic 2. Surgeon features in the haptic that allow for fluid (e.g., viscoelastic fluid) to be advanced or aspirated during the procedure act as a natural hinge, and leading haptic 4 will naturally bend at that location. The surgeon feature is described in more detail in the applications reference herein, but in general the surgeon feature is a region of decreased thickness relative to adjacent portions of the haptic that creates an opening between the optic and the haptic radially inner surface. As splay member 20 continues to be distally advanced, the distal end of leading haptic 4 continues to splay, as shown in FIG. 6, starting to extend generally in the distal direction. Continued splay member 20 advanced continues until finger 24 engages pocket 13 in the base, and further distal movement of splay member 20 is prevented. Leading haptic 4 is splayed in FIG. 7, with the free end of the haptic extending in the distal direction, and the haptic reconfigured to a splayed configuration. The trailing haptic can undergo a relatively minimal amount of deformation as the leading haptic is splayed, but is not considered to be splayed as that term is used herein. In FIG. 7 the trailing haptic is not yet splayed. In this embodiment the leading haptic is "actively" splayed into that an actuatable member makes direct contact with the free end of the haptic.

After the leading haptic is splayed, the IOL is then loaded into the cartridge, during which the trailing haptic is also splayed. In this embodiment the trailing haptic is passively splayed in that it is splayed as a result of a force being applied to a non-free end of the trailing haptic. The carrier base need not be moved relative to the cartridge at this point. Splay member 20 is not advanced any further to load the IOL into the cartridge, in this embodiment due to the stop 11 in the base.

Figure 9:
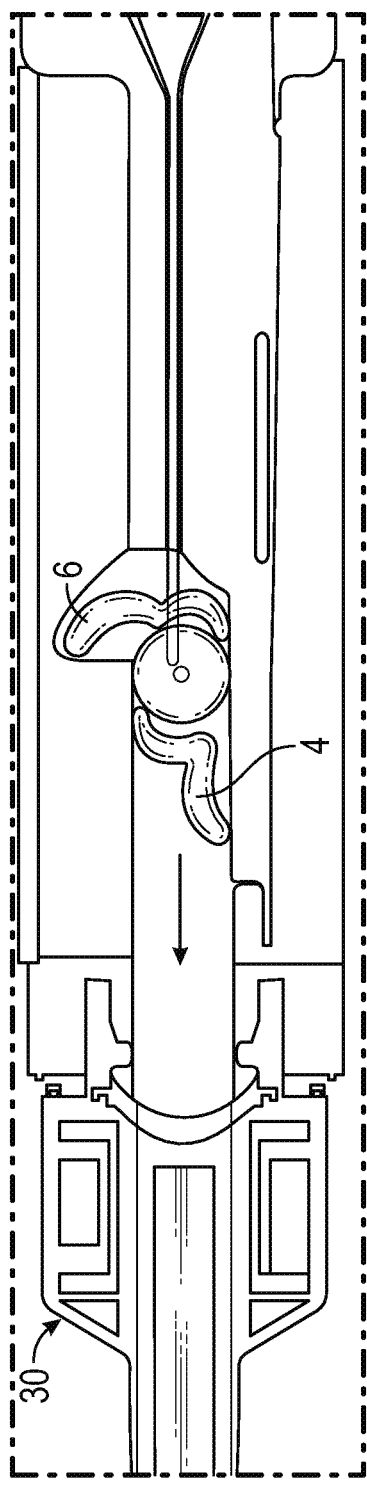
Figure 10:
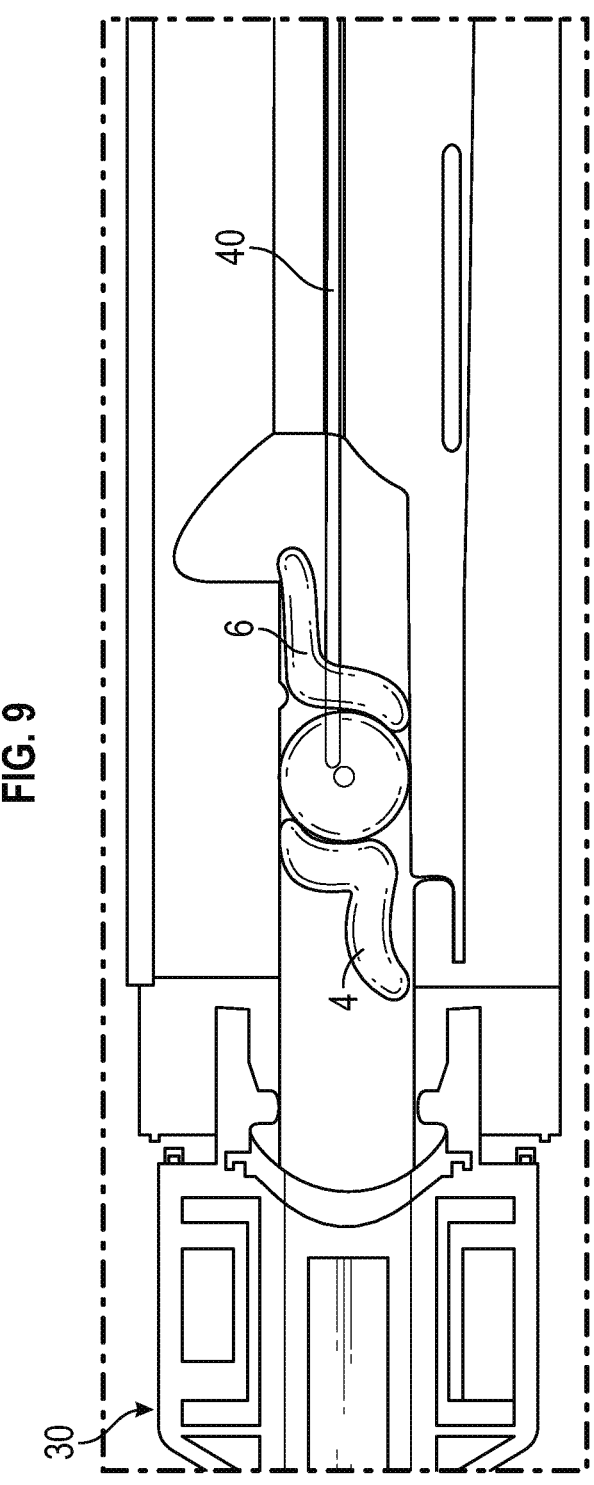
Figure 13:
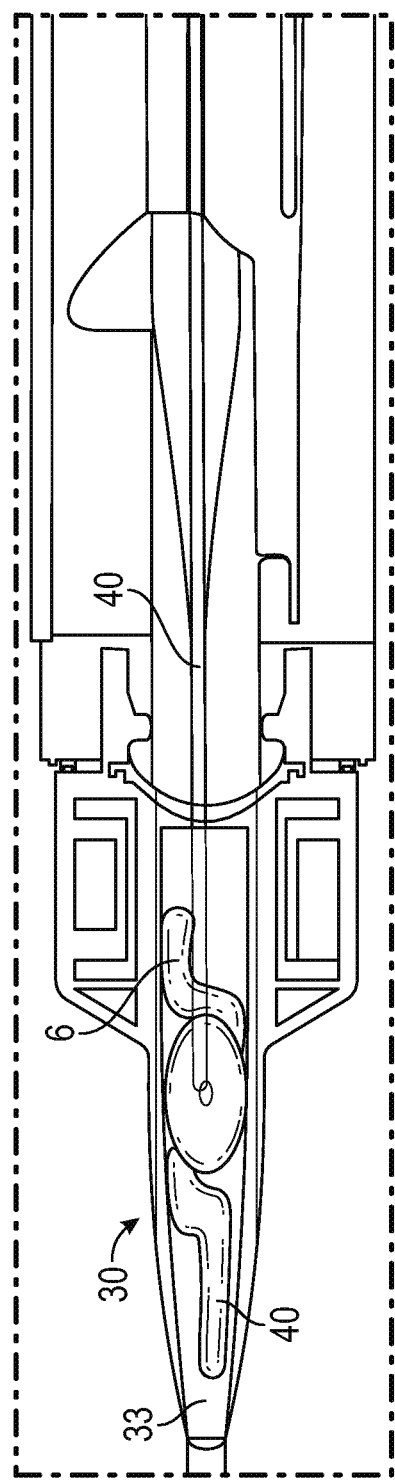

FIGS. 8-13 illustrate an exemplary loading process that loads the IOL into the cartridge after the leading haptic has been splayed. During the loading the trailing haptic is passively splayed. A loading member 40, which is optionally mechanically coupled to the splay member, is advanced distally within a channel or guide in the splay member, as shown in FIG. 8. Loading member 40 has an elongate distal portion sized and configured for advancement within and relative to the splay member channel. The distal end of loading member 40 is adapted to push the IOL into the cartridge (i.e., load the IOL into the cartridge). To load the IOL, the operator distally advances loading member 40, moving the IOL forward within carrier, as shown in FIGS. 9 and 10. During the loading process trailing haptic 6 is deformed against the channel wall as the IOL is advanced further down the carrier channel. In FIG. 10 trailing haptic 6 is significantly splayed proximally relative optic, and bends at the surgeon feature as described above in the context of the leading haptic. The free end portions of the haptics extend away from the optic portion, while the attachment portions of the haptics do not extend away from the optic portion as much. In these embodiments the free end portions are considered the portions distal to the bend locations of the haptics. As the IOL is about to be loaded into the cartridge, the leading haptic is distally splayed and the trailing haptic is proximally splayed. With the IOL shown, free end portions of each haptic are reconfigured. Loading member 40 continues to be advanced until the IOL is advanced into the cartridge delivery lumen, as shown in FIG. 13. As the IOL is loaded, the optic undergoes deformation due to a tapered surface of the cartridge. The haptics undergo additional reorientation relative to the optic as the IOL is advanced into the cartridge. Loading member 40 is sized so that the IOL is advanced to a predetermined position within the cartridge, to ensure it is advanced far enough but not out of the cartridge. A very small portion of the IOL could extend from the distal port of the cartridge. The operator then retracts the loading member within the carrier. The operator then removes the carrier from the cartridge to allow the positioning of other delivery devices, such as the delivery devices described in U.S. application. Ser. No. 13/835,876, filed Mar. 15, 2013. Optionally, an additional delivery member could be advanced through the carrier to deliver the IOL out of the cartridge.

Figure 14:
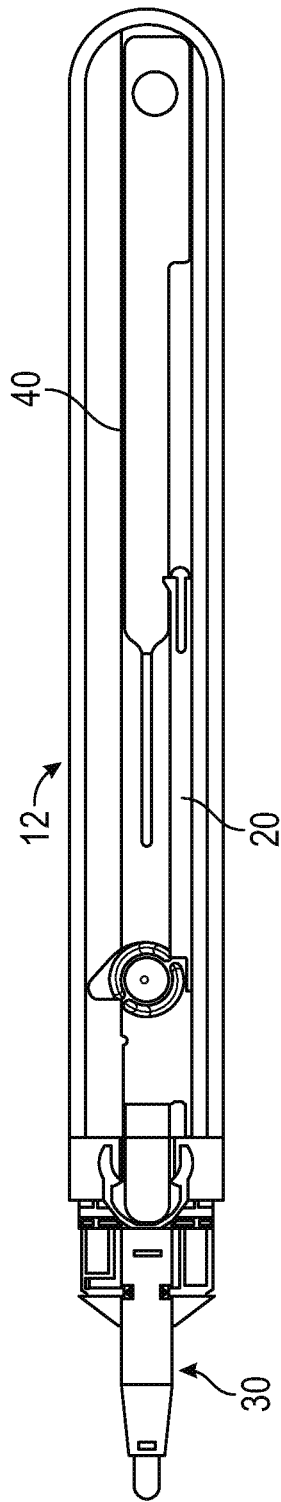
FIG. 14 illustrates an exemplary intraocular lens carrier and loading device.

FIG. 14 illustrates an additional embodiment of a carrier in which loading member 40 is disposed to the side of splay member 20 rather than axially moveable within it. Cartridge 30 is shown secured to the distal portion of the carrier base.

Embodiments below show a protective cartridge bay, or cartridge receiving area, included in the loading carrier base to allow the cartridge to be in the shipped assembly. The viscoelastic port (see FIG. 15) can be designed to mate to standard syringes and has a pathway that leads to proximity of the lens. The splay member and loading member can also be coupled to allow the operator to continue one motion to allow for splaying and loading of the IOL in one generally continuous act.

One or more components of the carrier can be, for example, machined white acetal copolymer, but can be any other suitable material. In alternative embodiments, a hand-held loading tool can be used in place of the integrated loading slide, and is an example of using additional components with the carrier base and splay slide.

FIGS. 16-32C illustrate exemplary embodiments of intraocular lens carriers that are adapted to store intraocular lenses, as well as to load intraocular lenses into a delivery device or delivery lumen. This disclosure generally refers to a delivery device (e.g., a cartridge) as a device that is different than the carrier, but the delivery device and carrier can be considered the same device in alternative embodiments. In those embodiments the intraocular lens can be loaded into a delivery lumen of the carrier. The carriers can be used to load an intraocular lens in either way. In the embodiment in FIGS. 16-32C they are separate components adapted to mate with one another. The carriers in FIGS. 16-32C are adapted to carry the exemplary accommodating intraocular lens in a stable, lightly axially-compressed condition (referred to herein as "compressed condition"). The intraocular lens can be carried in the compressed condition through, for example, sterilization, shipping, and storage. The carriers in FIGS. 16-32C are also adapted for touch-free loading of intraocular lenses into a delivery device for delivery in an eye.

Figure 16:
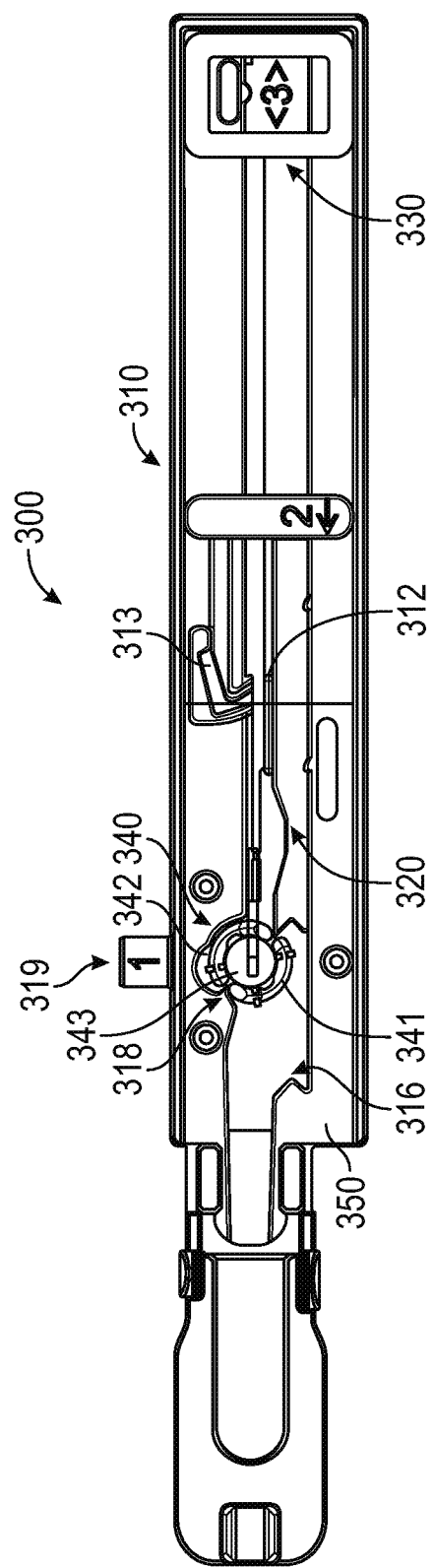
FIG. 16 illustrates an exemplary intraocular lens carrier and loading device.
Figure 17:
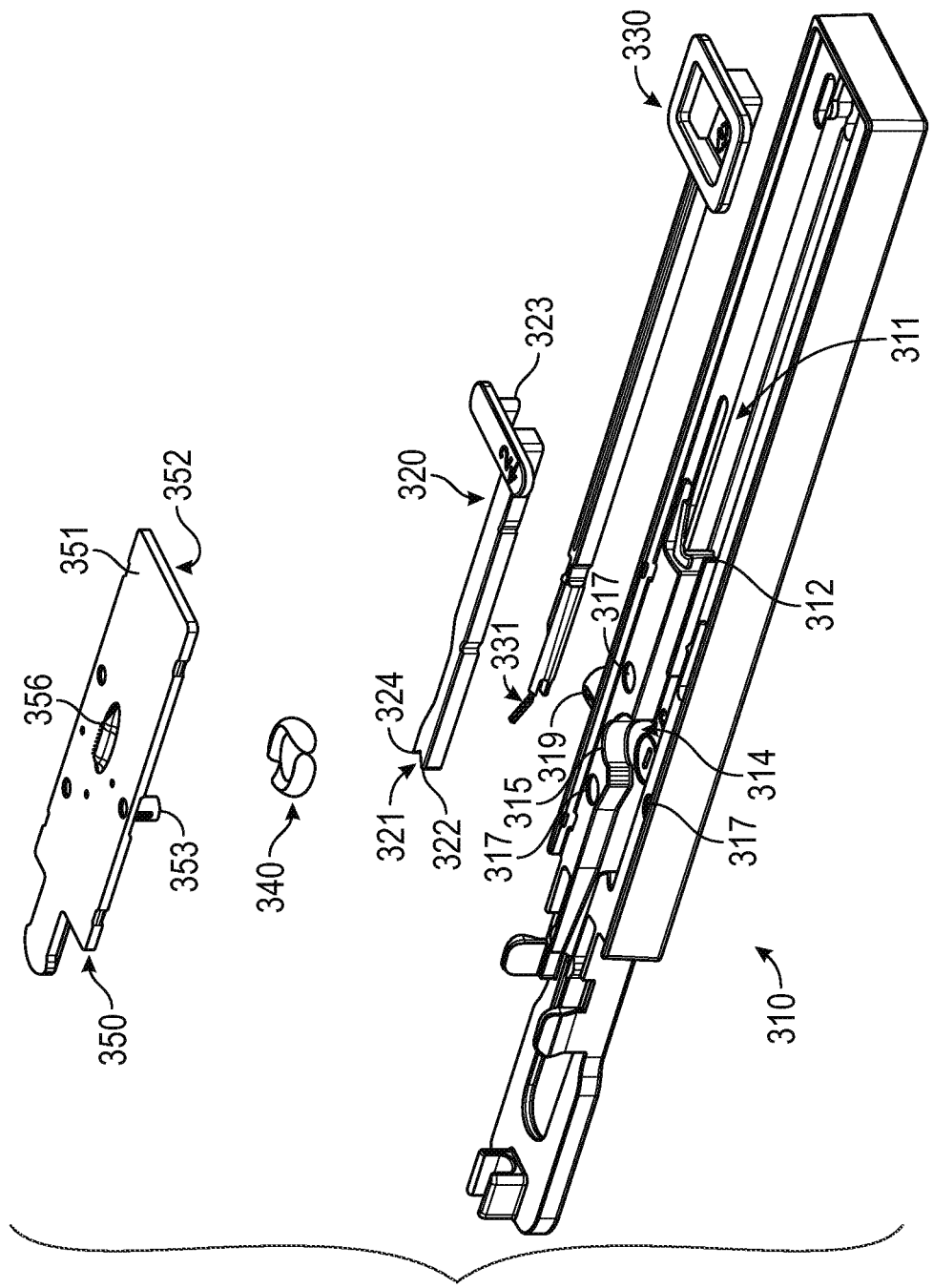
FIG. 17 is an exploded view of the intraocular lens carrier and loading device from FIG. 16.

FIG. 16 is a top view of an exemplary intraocular lens carrier. Carrier 300 includes base 310, splay member 320, load member 330, and lid 350. Lid 350 is shown as transparent to allow intraocular lens 340 to be seen between lid 350 and base 310. FIG. 17 shows an exploded view with base 310, load member 330, splay member 320, lens 340, and lid 350. Base 310 has a channel or guide 311 (see FIG. 17) in the proximal portion adapted to receive the proximal portions of load member 330 and splay member 320 therein. As shown in FIG. 16, splay member 320 and load member 330 include elongate portions that are positioned generally next to one another and extending in the proximal to distal direction (axially), while base 310 includes divider 312 that separates splay member 320 from load member 330. Splay member 320, load member 330, and channel 311 are all configured to allow splay member 320 and load member 330 to be moved distally within channel as part of the splay and loading process below. Base 310 also includes load member lock out 313 that prevents load member 330 from being advanced distally until release 323 of the splay member (see FIG. 17) engages and displaces lock out 313 radially, thus allowing load member 330 to then be advanced distally. This prevents distal movement of load member 330 until splay member 320 has been advanced far enough distally to ensure that the leading haptic is sufficiently splayed. Splay member 320 and load member 330 are somewhat similar in function to the other splaying members and pushing members set forth above in FIGS. 1-13. Base 310 also includes an intraocular lens receiving region 314 (see FIG. 17) that includes trailing haptic receiving area 315.

Splay member 320 in this embodiment has a distal portion 321 with a general forked, or branched, configuration. As shown in FIG. 17, distal portion 321 includes first extension 322 and second extension 324 of the branched configuration, with both extensions including first and second flat surfaces. The angle between the two branches of the branched configuration can be between about 60 degrees and about 120 degrees. If the angle is too large distal portion 321 may not index to the landing position after splaying. If the angle is too small distal end 321 may not be able to pick up the leading haptic at the beginning of the splay process. In the embodiment shown the angle is 90 degrees. In some embodiments the angle is between about 75 degrees and about 105 degrees. The branched configuration of distal portion 321 is configured to mate with splay member stop 316 (see FIG. 16) in base 310. Second extension 324 includes two flat surfaces, the flat surfaces defining an internal angle less than 90 degrees (such as 75 degrees or less, 60 degrees or less, or 50 degrees or less, such as about 45 degrees). The tip of second extension 324 is configured to, when splay member 320 is advanced distally, fit just between the free end of the leading haptic and the optic portion of lens 340. The positioning of extension 324 in this manner causes the leading haptic to start to splay when splay member is advanced, which is described in more detail below.

Figure 18:
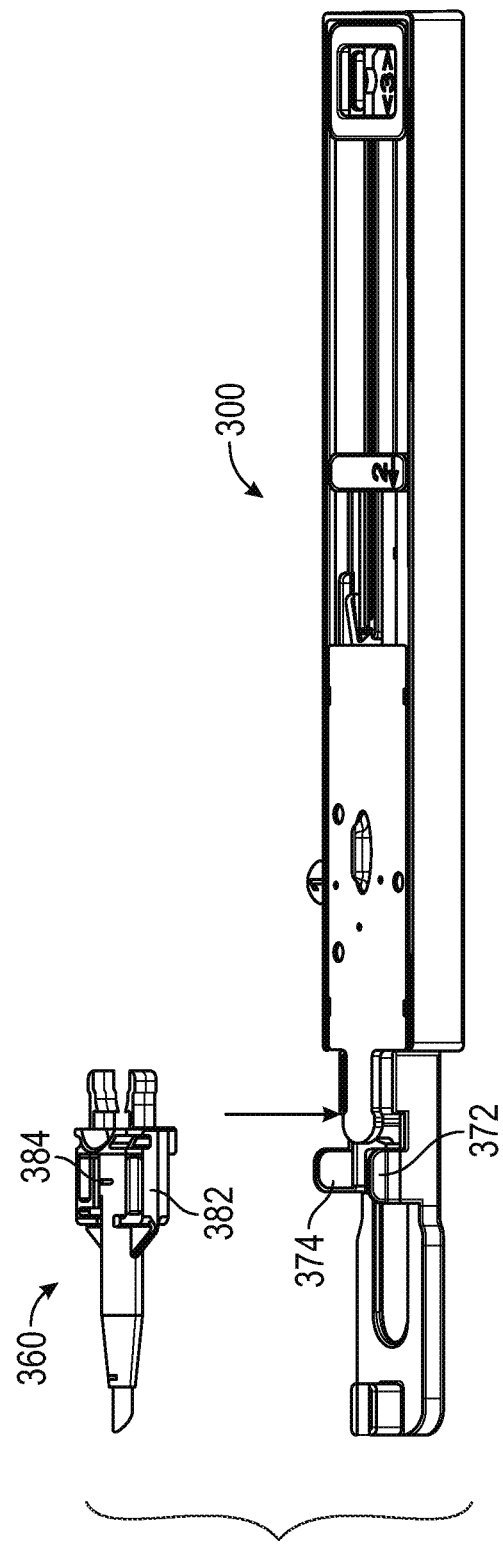
FIG. 18 is an exploded view showing an exemplary cartridge that can be secured to the exemplary carrier and loading device.
Figure 19:
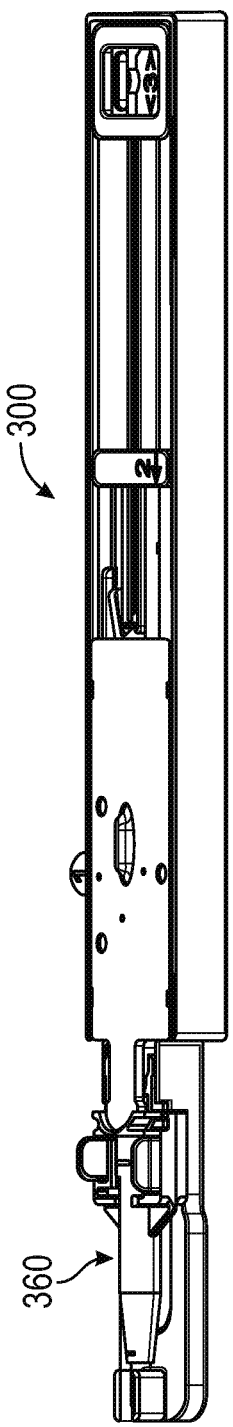
FIG. 19 shows the cartridge secured to the loading device.

FIG. 18 shows a perspective view of carrier 300 and cartridge 360 before the cartridge is secured to the distal cartridge receiving area of carrier 300. FIG. 19 shows the assembly after cartridge 360 is secured to the distal portion of carrier 300. In use, as will be described below, the intraocular lens is loaded from its receiving region in carrier 300 into a delivery lumen in cartridge 360.

Figure 20:
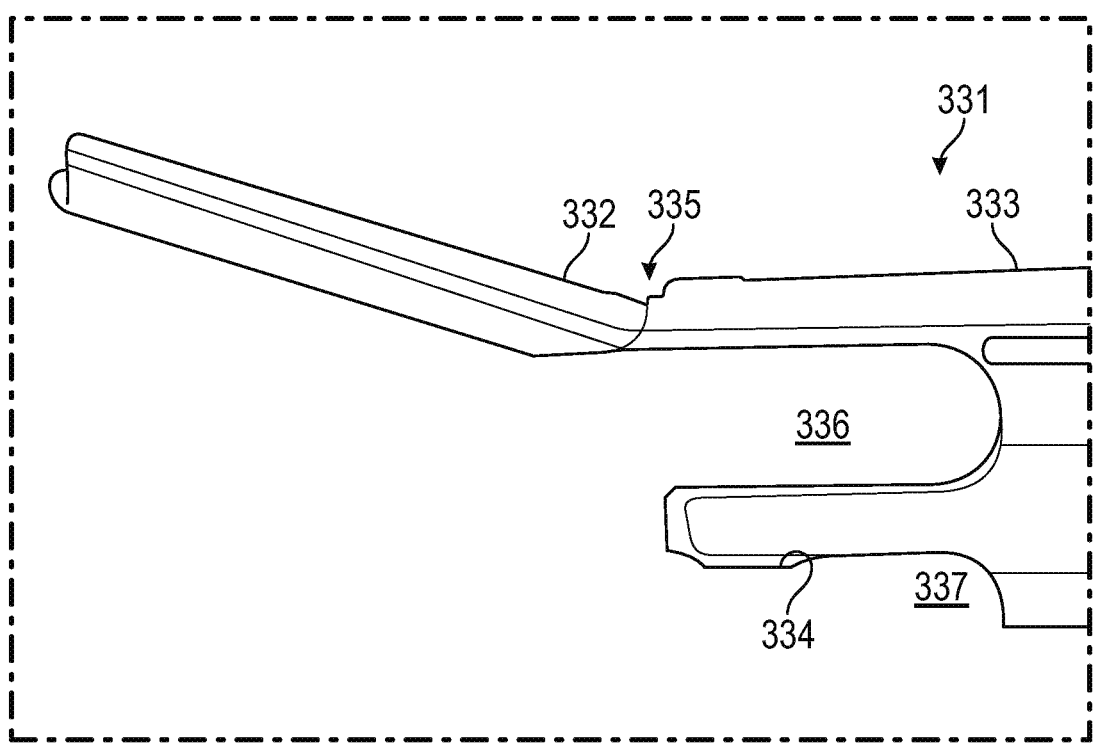
FIG. 20 shows an exemplary distal end of an exemplary loading member.

FIG. 20 illustrates distal end 331 of load member 330. Load member 330 includes an elongate body 333, a first extension 332 extending distally and in an upward direction relative to a top portion of elongate body 333 at a hinge 335. First extension 332 is adapted to rotate with respect to the portion of load body 333 proximal to extension 332 at hinge 335. Load body 333 also includes second extension 334 extending distally and in a generally linear orientation with respect to the proximal portions of load body 333.

FIG. 21 shows a view of bottom surface 352 of lid 350. Lid 350 is positioned on top of a portion of base 310, as shown in the exploded view in FIG. 24. Lid 350 covers the portion of base 310 where the lens 340 is positioned. Lid 350 includes a plurality of posts 353, which are adapted to fit within post guides 317 in base 310 (see FIG. 17) to help stabilize lid 350 with respect to base 310. In this embodiment there are three posts, although more or less can be used. It may be beneficial to use three posts, which develop a simple plane, whereas more posts may increase the risk of over constraint which could lead to increased variation in lens compression. Lid 350 also includes sight or probe apertures 354, which are described below. Lid 350 also includes a plurality of compression spokes 355 that extend downward (i.e., in the same direction as posts 353) from the bottom surface 352 of the lid. In this embodiment there are four compression spokes 355, and they have linear configurations extending radially away from the center of the lens receiving region.

Base 310 and lid 350 are adapted and configured to provide advantages when storing intraocular lens 340 for periods of time. Some types of accommodating intraocular lenses may be susceptible to undergoing power changes during storage due to, for example, degradation of IOL materials or forces on the lens from the packaging components. Eliminating or greatly reducing power changes during storage, or at least making them predictable, is highly desirable. For example, lens 340 can be a fluid-driven accommodating intraocular lens such as those incorporated by reference herein. For example, the two haptics may include fluid chambers in fluid communication with the option portion. If the haptics are compressed too greatly over time, fluid may transfer between the haptics and optics, causing power changes to the IOL. The compression spokes 355 of lid 350 provides a sufficient amount of compression to haptics to stabilize them without distorting them. The spokes also isolate interaction between the haptics and the carrier to the spokes, which prevents haptic compression coming from a larger surface such as the lid bottom surface. That is, the haptics are maintained in desired configurations so that the IOL power change is predictable during storage. The manner of controlling the degree of haptic compression in this embodiment uses an assembly method with finely controlled post height coupled with an equally controlled height of the lens compression feature, in this embodiment the spokes. The bottoming of the posts in the mating part of carrier base 310 controls a well-defined compression between a base surface on which the lens rests and the lens compression spoke. This compression holds the lens in a stabilized position through storage, which can include sterilization and shipping.

In this embodiment the posts are designed to sit on the plane of the base on which the haptics are disposed (in their respective pockets). This plane thus acts as a reference plane, or zero height. In some embodiments the haptics have a height of about 2.88 mm. Some haptics may have a designed height slightly greater than their actual height in the configuration in the base. In some embodiments the distance between the bottom of the spokes and the base surface on which the lens rests is between about 2.750 mm and about 2.850 mm. In some embodiments this distance is just less than the haptic height. In some embodiments the spoke height is about 0.200 mm. This distance isolates the interaction between the haptic and the carrier to the spokes alone and prevents compression coming from a larger surface.

The compression to the haptics is limited to locations on the haptic that result both in low deformation of the haptic and high holding stability. FIG. 22 illustrates the relative position of spokes 355 and haptics 341 and 342. IOL 340 includes an optic portion coupled to two haptics. Each of the haptics includes a buttress portion secured to the optic, as is described in the applications incorporated by reference. Two of the spokes each engage distal portions of the haptics. The other two spokes engage buttress portions of the haptics. Two of the spokes are disposed along the same imaginary line, while the other two spokes are disposed along the same imaginary line. The spokes are arranged so that they engage the same regions of each of the two haptics. The light compression stabilizes the power and quality of the lens through radiation or other sterilization processes as well as temperature changes or vibration effects of shipping. The light compression also holds the lens in position through the initiation of the splaying and loading sequences described herein.

The carrier is also adapted for lens compression verification. In this embodiment lid 350 includes probe or sight holes 354 (three are shown) that allow for the measurement of the compression level after the lens is in place within the base and the lid has been assembled onto the base. In some embodiments this can be performed by measuring the spoke to lens base gap through the lid and sight hole with a non-contact laser measurement system.

The carrier can also be adapted to enable verifying the intraocular lens quality or power during or after storage. This may be desirable in general, or in particular because some intraocular lenses have the potential to take on a very small permanent set through sterilization or due to aging, and thus there may be a need to verify quality and power change of the intraocular lens in the stored configuration.

One method of assessing the circularity of a reflected concentric ring pattern may be used to look at lens quality before or after compression of the lens. If this is to be done after the compression of the lens (e.g., after storage), the lid can be adapted with a window that would allow for this. In fact, the lid can include a plurality of windows (and/or the base could include one or more windows) and may be needed to allow for optical verification of the power and quality of the lens after being compressed.

FIGS. 23-31D illustrate examples of the lid and/or the base including one or more visualization windows formed therein. In embodiments in which at least one of the base and lid include one or more windows, one or more plugs should generally be included to complete the viscoelastic path for preparing to load the intraocular lens as well as for sealing the lens path for loading. Plugs can be shipped attached to the finished assembly, but in some embodiments the plugs are installed in the operating room just prior to loading to reduce the risk of disturbing the known compression.

Figure 23A:
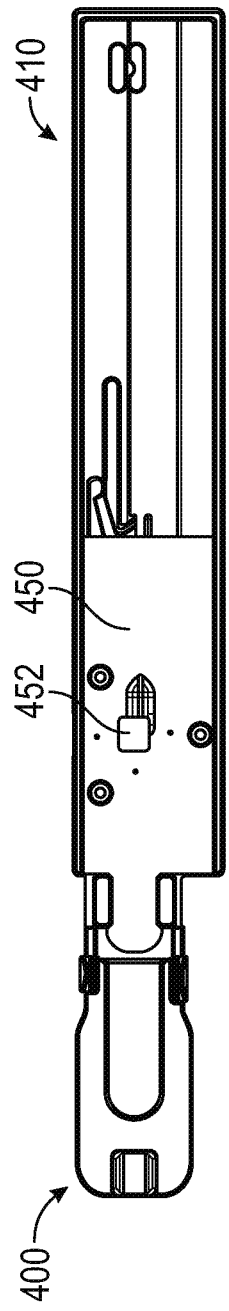
FIGS. 23A and 23B illustrate an exemplary carrier with bottom and top plugs.
Figure 23B:
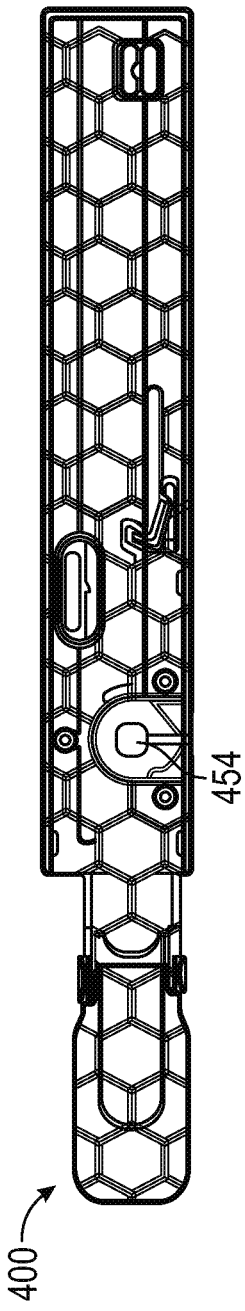
Figure 24:
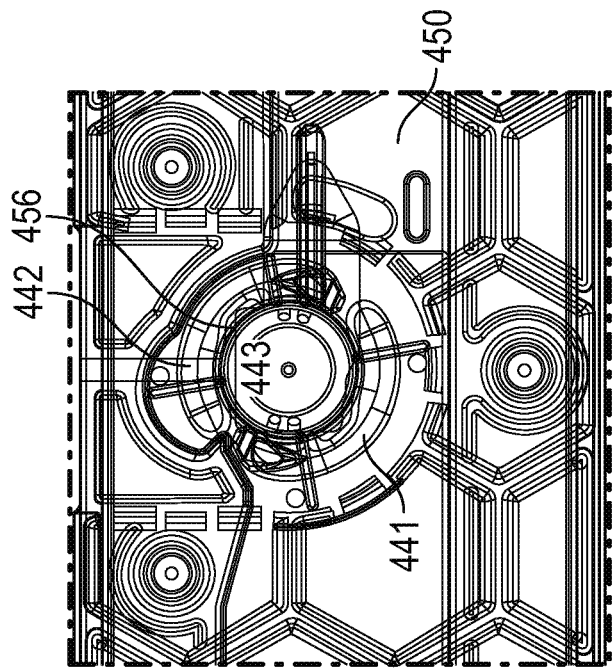
FIG. 24 is a top view with a top plug removed, with an optic portion visible through the window.

FIGS. 23A and 23B show top and bottom views, respectively, of exemplary carrier 400 that includes base 410 with a window and corresponding base plug 454, and lid 450 with a window and corresponding lid plug 452. Other components in the embodiments in FIGS. 16-22 are intended to be included in these embodiments even if not specifically mentioned herein. The plugs can be removed, respectively, to visualize the top or bottom of the IOL that is disposed inside the carrier. The windows are positioned within the lid and base in order to visualize the optic portion of the intraocular lens, as is shown in FIG. 24 with lid plug 452 removed. Lid 450 is shown as transparent to enable visualization of leading haptic 441, trailing haptic 442, and other components of the carrier. Optic portion 443 is viewed through window 456.

Figure 25A:
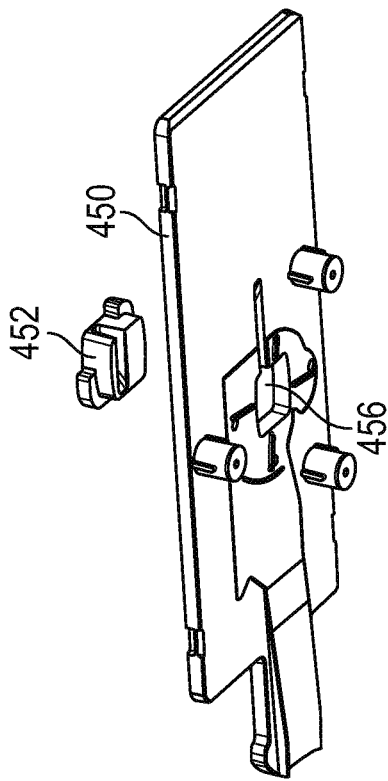
FIGS. 25A and 25B show top and bottom perspective exploded views of an exemplary lid with removable plug.
Figure 25B:
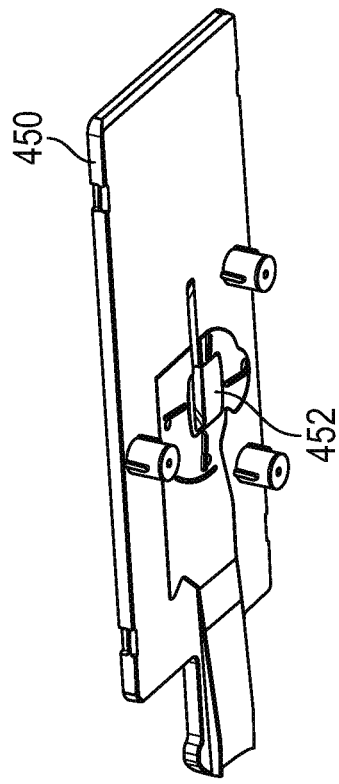
Figure 26A:
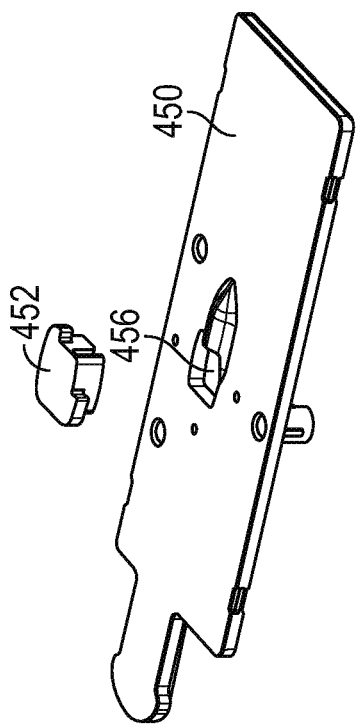
FIGS. 26A and 26B show top and bottom perspective views of an exemplary lid with removable plug secured thereto.
Figure 26B:
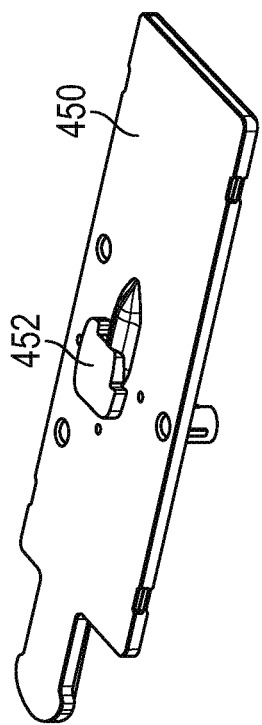

FIGS. 25A and 25B are perspective exploded top and bottom views, respectively, or lid 450, window 456 formed therein, and plug 452. Plug 452 includes a slot portion that is aligned with the slot in the bottom surface of the lid, as is described herein. FIGS. 26A and 26B show assembly views of FIGS. 32A and 32B.

FIGS. 27A-30 illustrate an exemplary embodiment of base 410 that includes a window on the bottom to allow visualization of the intraocular lens optic. Base 410 and base plug 480 are configured to mate and to be secured together so that window 412 can be plugged with plug 480. FIG. 27A shows a top perspective exploded view of base 410 and plug 480. FIG. 27B shows a close-up bottom perspective exploded view of base 410, including window 412, and plug 480. FIG. 28 is a perspective view of plug 480 showing fluid communication between fluid port 481 of plug 480, internal fluid channel 483, and outlet fluid port 482. The shape of the plug is shaped to mate with the base. Plug 480 is, in this embodiment, secured to base 410 with seven deformable locks 414, which are part of base 410. Only three of the locks 414 are labeled in FIG. 27B. FIG. 30 show a bottom view with plug in place to plug up the window, showing the locks 414 that hold plug in place. The plug can be removed by pulling on the fluid port 481 outer surface, in a downward direction. FIG. 29 shows the plug 480 and base 410 assembled, with outlet fluid port 482 in fluid communication with the inside of base 410. Plug 480 includes an element 484 (see FIG. 28) adapted to fit within window 412. In this embodiment they are circular, but could be a different shape. In this embodiment the base plug includes a fluid port, which will be described below in the context of the methods of use.

FIGS. 31A-31B show top and bottom assembled views of the lids, bases, and plugs in the embodiments in FIGS. 25A-30. FIG. 31A is a top view, while FIG. 31C is a top close-up view of plug 452. FIG. 31B is a bottom view, while FIG. 31D is a close-up of that view.

The disclosure also includes exemplary methods of loading an exemplary intraocular lens from any of the carriers herein into an exemplary cartridge, wherein the intraocular lens can be subsequently be delivered from the cartridge into an eye. The methods will be described generally without reference to specific parts of the devices herein, although examples will be given in the context of certain embodiments. Not all steps need necessarily be performed, and the order may vary. Before the IOL is loaded into the cartridge, however, the IOL may be stored in the carrier for any length of time. To prepare the IOL for storage, the intraocular lens is positioned in the IOL receiving region in the carrier base, such as IOL receiving region 314 shown in FIG. 17. The lid is then placed on top of the base, while positioning the posts in the post guides.

When the IOL is ready to be loaded in the cartridge (or other delivery device or delivery lumen), a cartridge can be secured to the carrier base, such as is shown in FIGS. 18 and 19. In FIGS. 18 and 19 carrier 300 includes mounting tabs 372 and 374 that are asymmetric. Tab 372 is longer than tab 374, both of which are adapted to engage with asymmetric apertures 382 and 384 in cartridge 360. This can help position the cartridge right side up, so that the bevel at the distal end of the cartridge is facing down when the IOL is delivered from the cartridge. The asymmetric tabs also protect the user from mounting the cartridge upside down, which would result in an inverted lens delivery.

After the cartridge is secured to the carrier base, a viscoelastic substance is then introduced through a side luer port of the carrier base to fill the lens chamber in the carrier base, which lubricates the lens and the loading path. An exemplary side port is port 319 shown in FIG. 16. Alternatively, tab 480 shown in FIG. 27A-30 can be the side port. A mark 399 (see FIG. 21) defined on the lid or base shows the correct volume of viscoelastic for use. Mark 399 as shown in FIGS. 21 and 22 is about a 30 degree arc.

As can be seen in FIG. 17, side port 319 is in fluid communication with an exit fluid port on the bottom of the base in the IOL receiving region, similar in configuration to port 482 in plug 480. The port conveys viscoelastic from a syringe or other viscoelastic delivery aid to the area around the IOL prior to the splaying and loading steps. The location of the fluid exit port that is nearest the lens should be positioned so that flow of the viscoelastic does not dislocate the IOL from its position prior to splaying and loading. In the embodiment in FIG. 17, the location of the exit port is at the center of the optic portion receiving area, however is could be moved to other locations, such as closer to the leading haptic. The size of this port can control the user's ability to create flow. In some embodiments the orifice diameter is about 0.010 in.

It is of note that the IOL is maintained in a position in which the leading haptic buttress shoulder, where the haptic is coupled to the optic portion, is in close proximity to the buttress traction pad on the base, such as buttress traction pad 318 shown in FIG. 16. This is generally important for stability of the IOL's position as the leading haptic is splayed.

The method of loading also includes splaying the leading haptic. FIGS. 32A-32C illustrate a sequence of loading the IOL from FIG. 16 (only a portion of the carrier is shown for clarity). In FIG. 32A the IOL is positioned in the carrier base just as is shown in FIG. 16. The free end of the leading haptic is proximally facing and is accessible in the proximal direction for direct contact and actuation. To initiate the leading haptic splaying, splaying member 320 is advanced distally within the carrier. Extension 324 on splaying member 320 is configured to fit between leading haptic 341 and optic portion 343 as splaying member 320 continues to be advanced distally. As splaying member 320 continues to be advanced distally, splaying member 320 engages leading haptic 341, bending leading haptic 341 away from optic portion 343 and towards the cartridge. Region 345 of leading haptic 341 is a thinner region of haptic 341 and is described in more detailed in the applications incorporated by reference herein. Region 345 acts similar to a living hinge, so that as splaying member 320 is advanced, haptic 341 will reliably bend at the hinge (see FIG. 32B). Splay member 320 is advanced until the distal end 321 engages splay member stop 316, as shown in FIG. 32B. In FIG. 32B leading haptic 341 has been splayed distally, and has been reoriented from the at-rest orientation (relative to the optic) in FIG. 32A to an orientation that extends away from the optic, and generally faces distally towards the cartridge delivery lumen.

As splaying member 320 is advanced and as it engages stop 316, release 323 will push lock-out 313 radially, allowing push member 330 to be advanced distally to load the IOL.

Push member 330 is then advanced distally within the carrier base as shown in FIG. 32C. Extension 332, which in an at-rest state extends slightly upward from body 333 (see FIG. 20) rides in slot 356 in lid 350 (see FIG. 17). Extension 332 is pressed over the top of the optic portion 343 by a descending ramp in the lid slot 356, as can be seen in FIG. 17. Positioning extension 332 over the optic portion adds axial stability to the optic for the force applied to the trailing buttress by the second extension 334 of the push member (see FIG. 20). Second extension 334 introduces a force to the trailing buttress, as can be seen in FIG. 32C, while stabilizing it so it does not shift under second extension 334 as it moves forward. Any trailing haptic material that slides under the second extension 334 into space 337 (see FIG. 20) during movement has ample clearance under second extension 334 and is protected from being pinched. Positioning the first extension 332 over the optic helps create the fold of the optic along the line of the first extension 332 as the IOL enters the tapering distal section of the carrier, as shown in FIG. 32C. Pusher member 330 continues to be advanced until the trailing haptic is splayed as well extending proximally away from the optic portion. Pusher member 330 continues to be advanced until the IOL enters into the cartridge, in the same general configuration as shown in FIG. 13. Method steps described above with respect to FIGS. 1-13 can also occur during the splaying and loading methods described with respect to FIGS. 32A-32C.

What is claimed is:

1. A device for loading an intraocular lens, comprising:
   a base member, comprising:
      an intraocular lens receiving region configured to house an intraocular lens, and
      a cartridge receiving region;
   a side port for receiving a fluid, wherein the side port is in fluid communication with the intraocular lens receiving region; and
   a cartridge configured to be coupled to the cartridge receiving region of the base member, wherein the cartridge is configured to receive the intraocular lens from the intraocular lens receiving region after the intraocular lens receiving region is lubricated by the fluid introduced through the side port.

2. The device of claim 1, further comprising a lid configured to cover at least part of the intraocular lens receiving region when coupled to the base member.

3. The device of claim 2, wherein the lid is configured to compress at least part of the intraocular lens when coupled to the base member.

4. The device of claim 2, wherein at least part of the lid is transparent.

5. The device of claim 2, wherein the lid comprises a window, wherein the window allows a power and lens quality of the intraocular lens to be assessed when the intraocular lens is housed within the intraocular lens receiving region.

6. The device of claim 5, wherein the window is configured to be covered by a lid plug.

7. The device of claim 1, wherein the side port is in fluid communication with an exit port in fluid communication with the intraocular lens receiving region, wherein the exit port is positioned such that the fluid entering through the side port and exiting through the exit port is conveyed to an area around the intraocular lens.

8. The device of claim 1, wherein the base member comprises a window, wherein the window allows a power and lens quality of the intraocular lens to be assessed when housed within the intraocular lens receiving region.

9. The device of claim 8, further comprising a base plug configured to cover the window, wherein the base plug comprises the side port.

10. The device of claim 1, wherein the fluid is a viscoelastic fluid.

11. A method of preparing an intraocular lens for delivery into an eye, comprising:
   introducing a fluid through a side port into an intraocular lens receiving region of a base member, wherein the intraocular lens receiving region is configured to house an intraocular lens; and
   loading the intraocular lens into a cartridge coupled to the base member using a loading member.

12. The method of claim 11, further comprising coupling a lid to the base member to cover at least part of the intraocular lens receiving region.

13. The method of claim 12, wherein the lid is configured to compress at least part of the intraocular lens when coupled to the base member.

14. The method of claim 12, wherein at least part of the lid is transparent.

15. The method of claim 12, wherein the lid comprises a window, wherein the window allows a power and lens quality of the intraocular lens to be assessed when housed within the intraocular lens receiving region.

16. The method of claim 15, further comprising covering the window with a lid plug.

17. The method of claim 11, wherein the side port is in fluid communication with an exit port in fluid communication with the intraocular lens receiving region, wherein the exit port is positioned such that the fluid entering through the side port and exiting through the exit port is conveyed to an area around the intraocular lens.

18. The method of claim 11, wherein the base member comprises a window, wherein the window allows a power and lens quality of the intraocular lens to be assessed when the intraocular lens is housed within the intraocular lens receiving region.

19. The method of claim 18, further comprising covering the window with a base plug, wherein the base plug comprises the side port.

20. The method of claim 11, wherein the fluid is a viscoelastic fluid.

* * * * *